United States Patent
Lan et al.

(10) Patent No.: US 12,370,282 B2
(45) Date of Patent: Jul. 29, 2025

(54) VENTILATION-TYPE UV LIGHT

(71) Applicant: Shenzhen Guanke Technologies Co., Ltd, Shenzhen (CN)

(72) Inventors: Qing Lan, Shenzhen (CN); Shoubao Chen, Shenzhen (CN); Bo Lei, Shenzhen (CN); Jinliang Lei, Shenzhen (CN)

(73) Assignee: SHENZHEN GUANKE TECHNOLOGIES CO., LTD, Shenzhen (CN)

( * ) Notice: Subject to any disclaimer, the term of this patent is extended or adjusted under 35 U.S.C. 154(b) by 705 days.

(21) Appl. No.: 17/746,486

(22) Filed: May 17, 2022

(65) Prior Publication Data
US 2023/0211037 A1    Jul. 6, 2023

(30) Foreign Application Priority Data
Dec. 31, 2021  (CN) .......................... 202123448115.1

(51) Int. Cl.
*A61L 9/20* (2006.01)
*F21V 33/00* (2006.01)

(52) U.S. Cl.
CPC ............ *A61L 9/20* (2013.01); *F21V 33/0096* (2013.01); *A61L 2209/11* (2013.01); *A61L 2209/12* (2013.01); *A61L 2209/134* (2013.01)

(58) Field of Classification Search
CPC .... A61L 9/20; A61L 2209/11; A61L 2209/12; A61L 2209/134; A61L 2209/10; F21V 33/0096; F21V 23/06; F21V 23/008; F21V 17/02; F21V 21/044; F21V 33/0064; F21V 17/12; F21V 33/0088; F24F 13/078; F24F 8/22; F21K 9/23; F21S 8/026; F21S 8/061; F21Y 2103/33; F21Y 2107/30; Y02A 50/20
USPC ..................................... 250/504 R
See application file for complete search history.

(56) References Cited

U.S. PATENT DOCUMENTS

| 10,865,977 | B1 * | 12/2020 | Lan | ......................... F21V 29/67 |
| 2005/0111234 | A1 * | 5/2005 | Martin | .................... F21V 29/77 |
| | | | | 362/555 |
| 2013/0135868 | A1 * | 5/2013 | Xue | ........................ F21V 29/78 |
| | | | | 362/249.02 |

FOREIGN PATENT DOCUMENTS

WO    WO-2021049766 A1 *  3/2021 ........... F04D 25/088

* cited by examiner

*Primary Examiner* — Michael Maskell
(74) *Attorney, Agent, or Firm* — Maier & Maier, PLLC

(57) ABSTRACT

A ventilation-type UV light includes a light body, an air guide structure provided at the bottom of the light body, a UV module, a fan and two air inlets; the air guide structure and the light body enclose to form a mounting space, the UV module is installed inside the mounting space; the fan is provided inside the air guide structure, the bottom of the air guide structure is provided with air outlets, the air inlets are provided on the periphery or bottom of the ventilation-type UV light in an encircling way, and both the air inlets and the air outlets access the mounting space. Air can flow into the mounting space along the air inlets and then can be discharged downward via the air outlets after being sterilized and disinfected by the UV module in the mounting space.

10 Claims, 33 Drawing Sheets

VENTILATION-TYPE UV LIGHT

BACKGROUND

Technical Field

The present disclosure relates to light source devices field, and especially relates to a ventilation-type UV light.

Background

UV lights can sterilize and disinfect air around the light body well, but cannot sterilize and disinfect air away from lights well. By applying a fan to the UV light, exchange of sterilized air around the light and air to be sterilized away from the light can be promoted, so as to expand the sterilization scope of the UV light. In relevant art, the ventilation efficiency of external air of the UV light is low, and the sterilization scope is small. Its restricting factors include:

(1) Lights usually adopt a small-power fan, if the ventilation efficiency is improved by increasing the power of the fan, high noises will be generated, and the service will be affected; after the fan power is increased, its volume will increase accordingly, while the size of lights is usually small, and it is not suitable for installing a large-size fan.

(2) The incoming and outgoing air directions of the fan are unreasonable. As a result, the fan usually can drive air convection within 1 m, it is easy to generate an area without air convection or slow air flow in the position nearby the outside of the light and away from the air inlets and air outlets, and the air circulation effect is poor.

(3) When designing the UV sterilization structure, to improve the service safety, it usually needs to design a complex structure to prevent leakage of UV rays. As a result, the light structure is complex, and the volume is big, which further affects the performance realization of the fan.

(4) Air flow outside the light will be interfered mutually during ventilation.

In addition, when the radial dimension of the downlight in relevant art is fixed, the downlight can only be installed in a mounting hole whose dimension is applicable to the radial dimension of the downlight, limiting the application scenarios of the downlight.

The foregoing content is only used for assisting in understanding the technical scheme of this invention, but does not mean the acknowledgement of that the above content is the current technology.

SUMMARY

To solve the above problems, the present disclosure mainly aims to provide a ventilation-type UV light to improve the ventilation efficiency of external air of the ventilation-type UV light, enlarge the sterilization scope of the light, avoid mutual interference of external air during working of the light and simplify the structure of the ventilation-type UV light. In addition, the present disclosure also provides a proposal where the downlight can be installed in different types and sizes of mounting holes to expand the mounting scenarios of the downlight.

To realize the above purpose, the present disclosure provides a ventilation-type UV light that comprises the light body, an air guide structure provided at the bottom of the light body, a UV module, a fan and two air inlets; the air guide structure and the light body enclose to form a mounting space, the UV module is installed inside the mounting space; the fan is provided inside the air guide structure, the bottom of the air guide structure is provided with air outlets, the air inlets are provided on the periphery or bottom of the ventilation-type UV light in an encircling way, both the air inlets and the air outlets access the mounting space;

wherein, air can flow into the mounting space along the air inlets and then can be discharged downward via the air outlets after being sterilized and disinfected by the UV module in the mounting space.

Other characteristics and corresponding beneficial effects of the present disclosure invention are elaborated in the latter part of the specification.

The solving ideas of technical problems of the present disclosure invention and relevant product design solutions are as shown below:

Based on the mounting mode of conventional lights, a fan and a UV module are provided inside the light, the air inlets and air outlets of the light are designed in a new way, to make air flow into the light via the air inlets along the periphery of the light, and sterilized air is discharged downward via the air outlets at the bottom of the light under the action of the fan and the air guide structure after sterilization and disinfection of the air. Such a ventilation proposal for incoming and outgoing air can form air convection in the up-down direction in the working space of the light, and accelerate air convection between the upper space and the lower space. The air flow scope in the up-down direction is also the effective sterilization scope of the light. The air inlets of such a ventilation-type UV bulb are provided on the periphery of the light, which enables air to flow into the light stably from the lateral side of the light within 360° and enlarges the horizontal sterilization scope; air outlets are provided at the bottom of the light, which enables air to be discharged rapidly from the bottom air outlet under the compression of the fan and the air guide structure, significantly enlarging the vertical sterilization scope of the light. Compared with lights with the UV sterilization function in prior art, such a ventilation-type UV bulb can significantly improve the ventilation efficiency and effective sterilization scope of external air, and when several ventilation-type UV lights are provided within the sterilization space, convection in the up-down direction can be realized between adjacent lights to realize ventilation, air flow and circulation will not be interfered mutually, lights can be laid out conveniently during installation, and it is easy to realize dead zone-free sterilization and disinfection of the sterilization space.

In addition, the air guide structure can change the incoming and outgoing air directions and can also increase the flow rate of air when it is discharged out of the light by reducing the size of the air outlets, so that air can be discharged downward to a further place rapidly and air convection beyond 1 m can be driven.

Therefore, under the premise of safety use of UV rays, such a new ventilation structure can significantly improve the air ventilation efficiency of the UV light, enlarge the sterilization scope of the light and especially achieve a good sterilization effect in the lower space nearby the ground; and the structure of the proposal is simple, the convenience of manufacture and installation can be improved, and the practical value of the present disclosure invention is relatively high. The relevant implementation proposal is elaborated in the rear part of the summary.

In addition, the present disclosure also relates to a new downlight mounting structure. the downlight comprises the light body and at least two mounting subassemblies, the mounting subassemblies comprise a fixed plate, engaging lugs and clamping pieces, the fixed plate is provided on the surface of the top of the light body horizontally in a slidable way and can be located for fixing corresponding to the light body, the engaging lugs and the fixed plates are directly or indirectly connected, and the clamping pieces are elastic parts installed on the engaging lugs. With the flexibly provided mounting subassemblies, the downlight can be installed in different types and sizes of mounting holes.

Wherein, the definition and characteristics of the above different types of UV lights are as follows:

(1) Built-in UV light: Such lights inhale air into the enclosed light cavity via the fan, after UV sterilization and disinfection in the light cavity, sterilized air is exhausted out of the light to finish air sterilization and disinfection and ventilation. They are mainly used for air disinfection. People do not need to leave the sterilization place when such lights are working, so people can be protected from the damage of UV light, man-machine symbiosis can be realized, and the safety performance is high.

(2) Upper-layer horizontal emission UV light: By installing the UV light in the upper space 2.1 m above the ground or floor, the UV light can horizontally emit UV rays to the outside of the light to sterilize and disinfect the upper space. During disinfection of the light, people can carry out activities in the lower space below 2.1 m, and do not need to leave the sterilization occasion, and the safety performance is high.

Declaration: The sterilization or disinfection in the present disclosure invention generally refers to UV sterilization or disinfection.

BRIEF DESCRIPTION OF THE DRAWINGS

Many aspects of the embodiments can be better understood with reference to the following drawings. The components in the drawings are not necessarily dawns to scale, the emphasis instead being placed upon clearly illustrating the principles of the embodiments. Moreover, in the drawings, like reference numerals designate corresponding parts throughout the several views.

Figure 1:
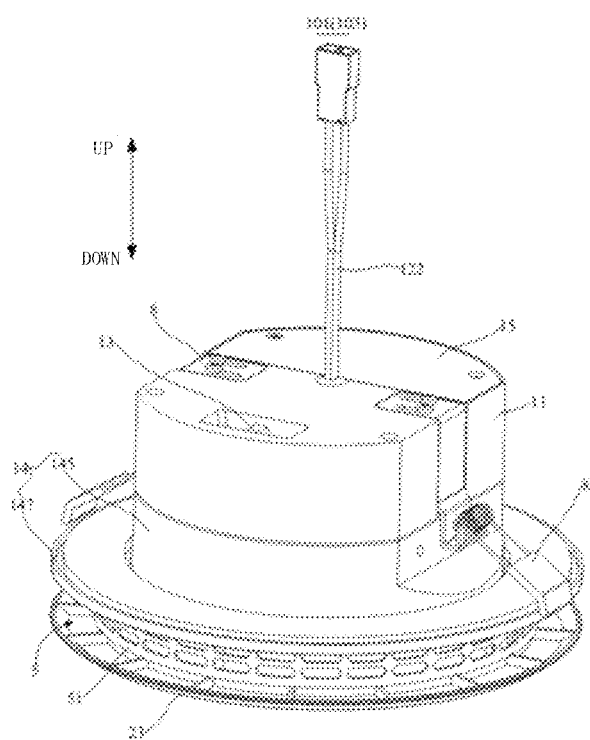
FIG. 1 is a schematic diagram showing the structure of one perspective of one embodiment of the ventilation-type UV downlight in the present disclosure.
Figure 2:
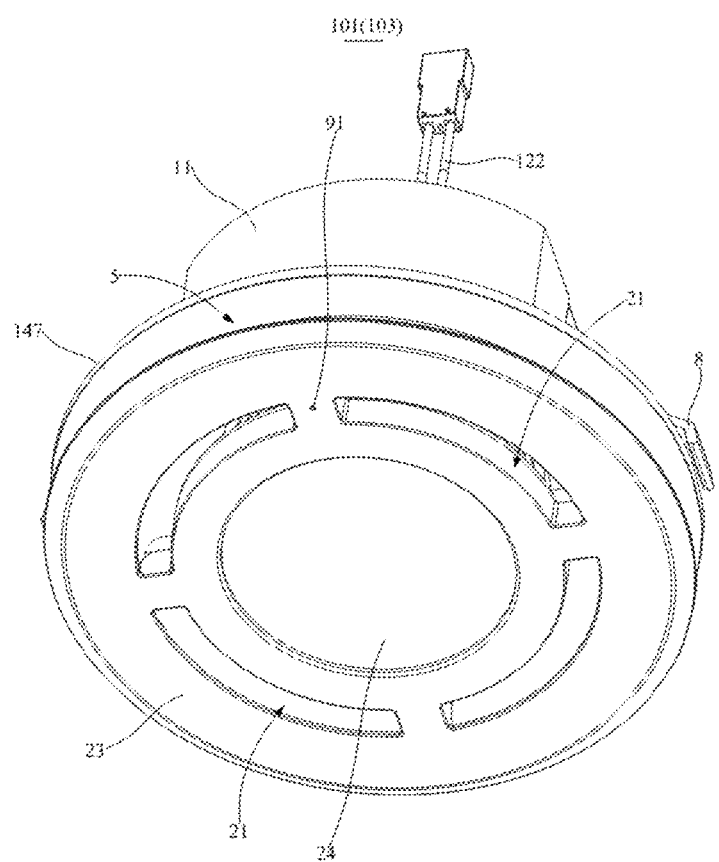
FIG. 2 is a schematic diagram showing the structure of another perspective of the new-type ventilation-type UV downlight in FIG. 1.

The shape, dimension, proportion or position relationship of parts of the product in drawings may be real data of embodiments and they are under the protection of the present disclosure invention.

DETAILED DESCRIPTION

To make the objective, technical solutions and advantages of the present disclosure invention clearer and be understood better, further detailed descriptions of embodiments of the present disclosure invention are made in combination with drawings. Understandably, the specific embodiments described are just used to explain but not limit the present disclosure invention.

According to FIGS. 1-31, the present disclosure relates to several types of ventilation-type UV lights 101 containing the same ventilation structure. The ventilation-type UV light 101 can be ventilation-type UV downlight 103, ventilation-type UV mining lamp 105, ventilation-type UV corn lamp 107, ventilation-type UV ceiling light or ventilation-type UV bulb 109.

Figure 3:
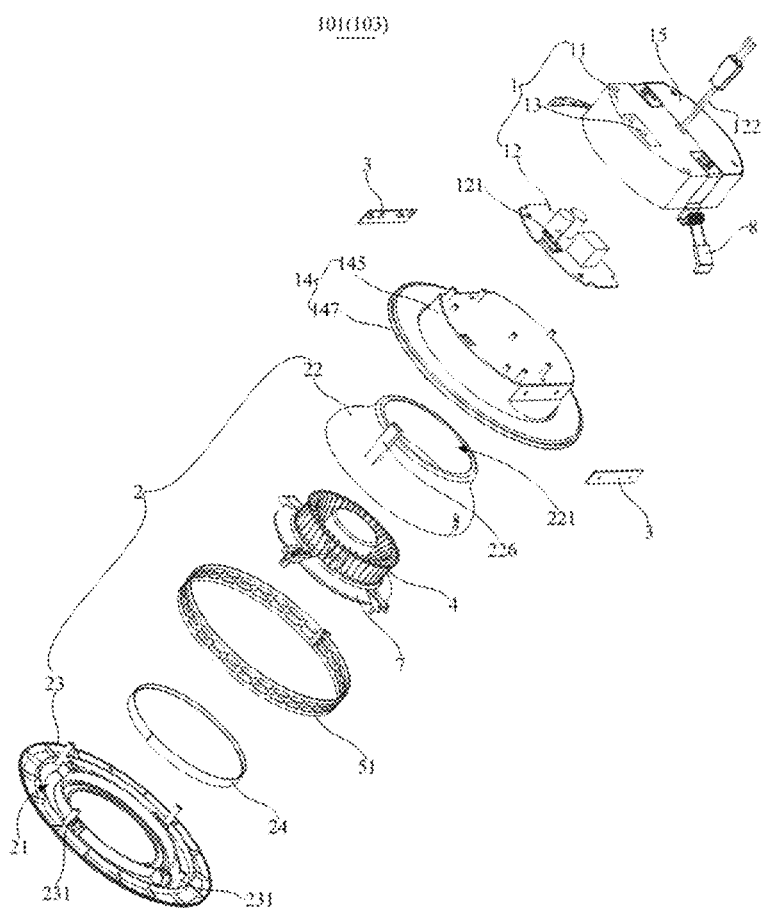
FIG. 3 is a schematic diagram showing the explosion structure of the ventilation-type UV downlight in FIG. 1 from one perspective.
Figure 4:
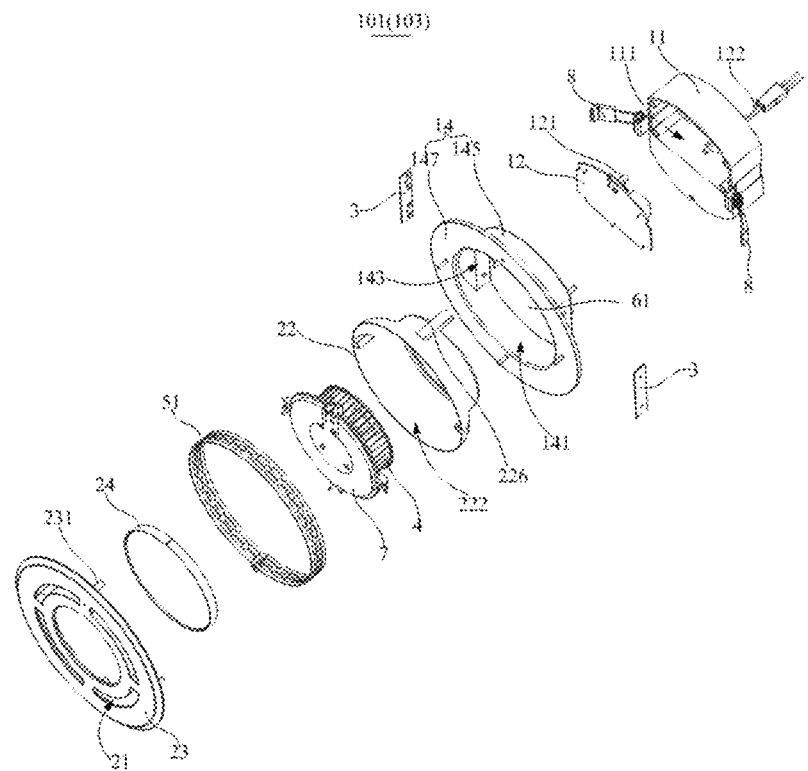
FIG. 4 is a schematic diagram showing the explosion structure of the ventilation-type UV downlight in FIG. 1 from another perspective.
Figure 5:
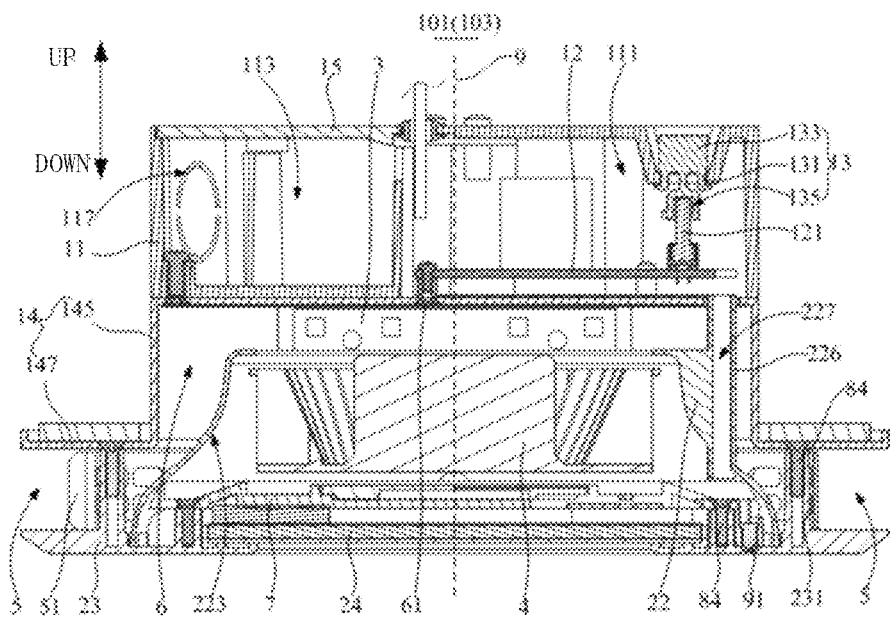
FIG. 5 is a diagrammatic cross section of ventilation-type UV downlight in FIG. 1.

According to FIGS. 3-5, in one embodiment of the present disclosure, the ventilation-type UV light 101 comprises the light body 1, an air guide structure 2 provided at the bottom of the light body, a UV module 3, a fan 4 and two air inlets 5; air guide structure 2 and light body 1 enclose to form a mounting space 6, UV module 3 is installed inside mounting space 6; fan 4 is provided inside air guide structure 2, the bottom of air guide structure 2 is provided with air outlets 21, air inlets 5 are provided on the periphery of ventilation-type UV light 101 in an encircling way, both air inlets 5 and air outlets 21 access mounting space 6; wherein, air can flow into the mounting space 6 via the air inlet 5, can be discharged downward via the air outlet 21 after sterilization and disinfection by the UV module 3 in the mounting space. In addition, when the bottom of light body 1 is provided with a groove 141 with a downward opening, the air guide structure 2 can be installed inside the groove, and the air inlet 5 is formed by the air guide structure 2 and the groove 141 at the bottom of light body 1. In other words, air inlets 5 can be provided at the bottom of ventilation-type UV light 101 and on the outside of air outlet 21.

Wherein, light body 1 can serve as the main body of ventilation-type UV light 101, to facilitate installation of parts of ventilation-type UV light 101 like air guide structure 2. Also, according to the structure of light body 1, the type of the ventilation-type UV light 101 can be the aforethe ventilation-type UV downlight 103, ventilation-type UV mining lamp 105, ventilation-type UV corn lamp 107, ventilation-type UV ceiling light, ventilation-type UV bulb 109, etc. Air guide structure 2 and light body 1 can enclose to form a mounting space 6 for installing UV module 3, so that when the air flows into the mounting space 6 via the air inlet 5, the UV module 3 provided inside the mounting space 6 can emit UV rays to sterilize and disinfect air inside the mounting space 6. Wherein, to improve the convenience of installation, repair and replacement of the air guide structure 2, the air guide structure 2 can connect to light body 1 in a dismountable way. For example, air guide structure 2 can be fixed onto light body 1 via screws or clamps. UV module 3 can be UV LED lights or gas discharge UV tubes. Fan 4 can provide the driving force and drive external air to enter mounting space 6 via air inlet 5, and then external air is exhausted via air outlet 21 to form a flow path, so that external air can flow via air inlet 5 of ventilation-type UV light 101 into mounting space 6 for sterilization and disinfection by UV module 3, and then sterilized and disinfected air is discharged downward via air outlet 21.

According to FIGS. 3-5, in one embodiment of the present disclosure, air guide structure 2 comprises a wind scooper 22 and a baseplate 23, wind scooper 22 is a tubular structure with an opening at each end, the top port 221 and bottom port 222 of wind scooper 22 access each other, top port 221 accesses mounting space 6, baseplate 23 is provided at the bottom of wind scooper 22, the corresponding bottom port 222 is provided with a downward air outlet 21 to make air that flows into mounting space can pass through top port 221 and bottom port 222 and then can be discharged via air outlet 21.

In this embodiment, air guide structure 2 is composed of the tubular wind scooper 22 and plate-type baseplate 23. The air guide structure 2 can be relatively simple, to improve the processing convenience of this air guide structure 2. Wherein, wind scooper 22 and baseplate 23 can be an integral structure. Of course, they can be provided separately. In such a case, wind scooper 22 and baseplate 23 can be connected in a dismountable way (via screws and other fasteners 84) to improve the installation convenience of fan 4 inside air guide structure 2. Wind scooper 22 can be placed horizontally, so that air guide structure 2 can be installed conveniently and air can be discharged downward better. Baseplate 23 can be circular, square or in other shapes, that is, baseplate 23 can be in any shape.

According to FIG. 5, in one embodiment of the present disclosure, wind scooper 22 also comprises an air guiding plane 223 provided between top port 221 and bottom port 222, and air guiding plane 223 extends to the air outlet 21. Air guiding plane 223 is on the inner sidewall of wind scooper 22 and provided in the arc shape. It can be used for air diversion and air compression. Further, wind scooper 22 can also comprise a connecting part 226 higher than top port 221 and against the lower surface of light body 1, and the inside of connecting part 226 is provided with a through-hole 227. In such a case, the connecting part 226 can be used for passing through of the lead to prevent the lead from being damaged by UV rays, and increase the height of air inlets 5. In one embodiment of the present disclosure, fan 4 can be centrifugal fan 4 that enables air to flow into the fan from one end and flow out of the fan from the periphery, and can be provided horizontally inside wind scooper 22. In such a case, the air inlet 5 of fan 4 is corresponding to the top port 221. The bottom of fan 4 can be provided with a shielding part 7 for preventing leakage of UV rays, and the size of shielding part 7 is larger than top port 221 and smaller than bottom port 222. In other words, three projections of the bottom port 222, the shielding part 7 and the top port 221 on the horizontal plane are provided in the descending order. Wherein, shielding part 7 can be an independent part; or component, e.g. bottom lighting module 24 used for providing the lighting function; also shielding part 7 and baseplate 23 can be an integral structure, that is shielding part 7 is one partial structure of baseplate 23. In addition, air outlet 21 can be provided on baseplate 23 and between the periphery of bottom port 222 and shielding part 7. In other words, air outlet 21 can be provided along the periphery of the shielding part 7 in an encircling way, preventing UV rays leaking from air outlet 21 to the outside of ventilation-type UV light 101; at the same time, such arrangement can also enlarge the coverage of air outlet 21, preventing concentration of air outlets 21 in one position. Further, ventilation-type UV light 101 has a center line 9 in the up-down direction, center line 9 is in the center of light 101, and passes through the light body 1, air guide structure 2 and the fan 4, air inlets 5 can also be provided around the center line 9. Specifically, air inlet 5 can be formed through enclosing of the periphery of light body 1 and periphery of air guide structure 2 and can make air flow into mounting space 6 horizontally, obliquely upward or obliquely downward via the air inlet 5. When the fan 4 works, air is inhaled via top port 221 and discharged from the periphery of fan 4 to air guiding plane 223 of wind scooper 22 and then blown to air outlet 21 via air guiding plane 223, and finally discharged rapidly via the bottom air outlet 21 through compression on the air guiding plane 223 and via the air outlet 21. Further, to facilitate users to know the working status 3 of the UV module (FIG. 2 and FIG. 5), this air guide structure 2 also comprises an indicator light 91 used for displaying the working status of UV module 3. At the same time, at least part of structure of the indicator light 91 is exposed to the bottom surface of the air guide structure 2, facilitating observation of the user.

Figure 6:
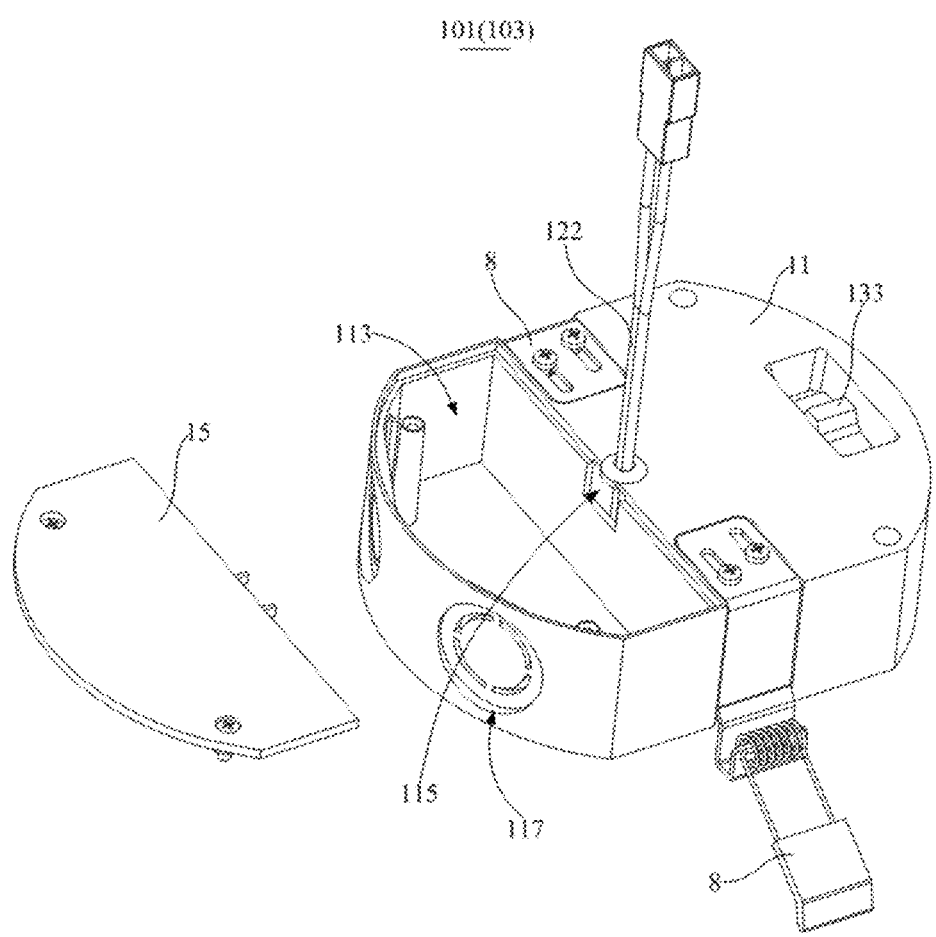
FIG. 6 is a schematic diagram showing the explosion structure of the control box of the ventilation-type UV downlight in FIG. 1 from one perspective.
Figure 7:
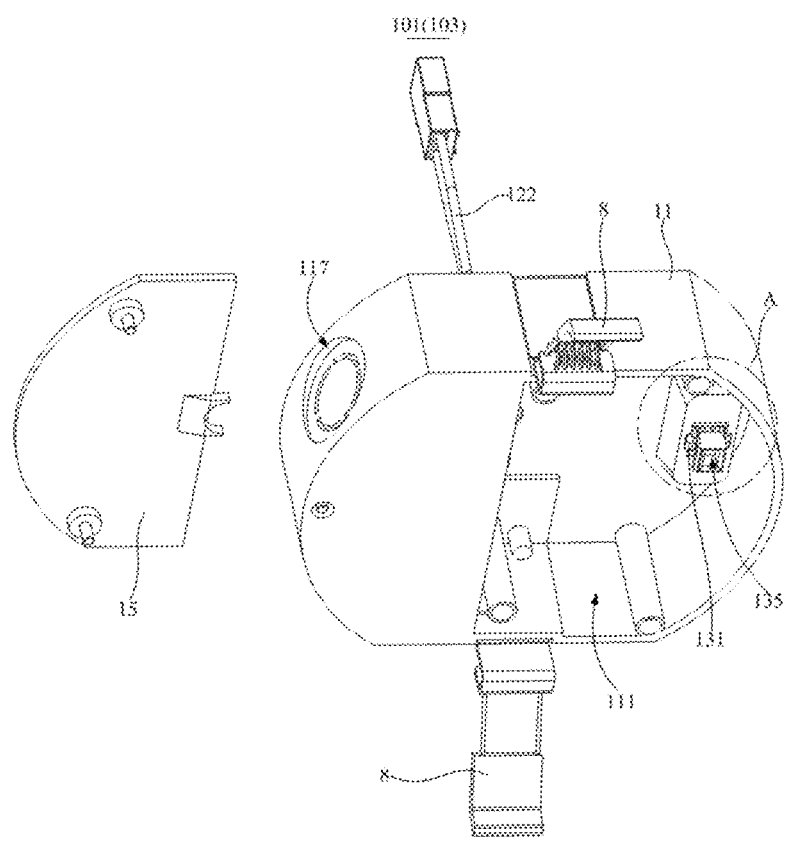
FIG. 7 is a schematic diagram showing the explosion structure of the control box of the ventilation-type UV downlight in FIG. 1 from another perspective.
Figure 8:
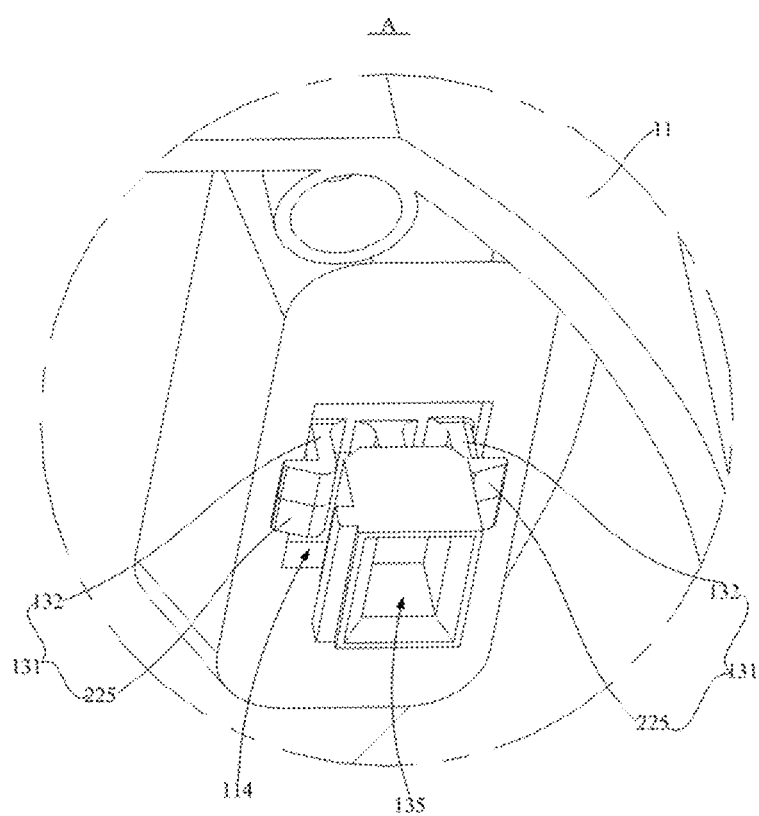
FIG. 8 is a local enlarged schematic of section A in FIG. 7.
Figure 9:
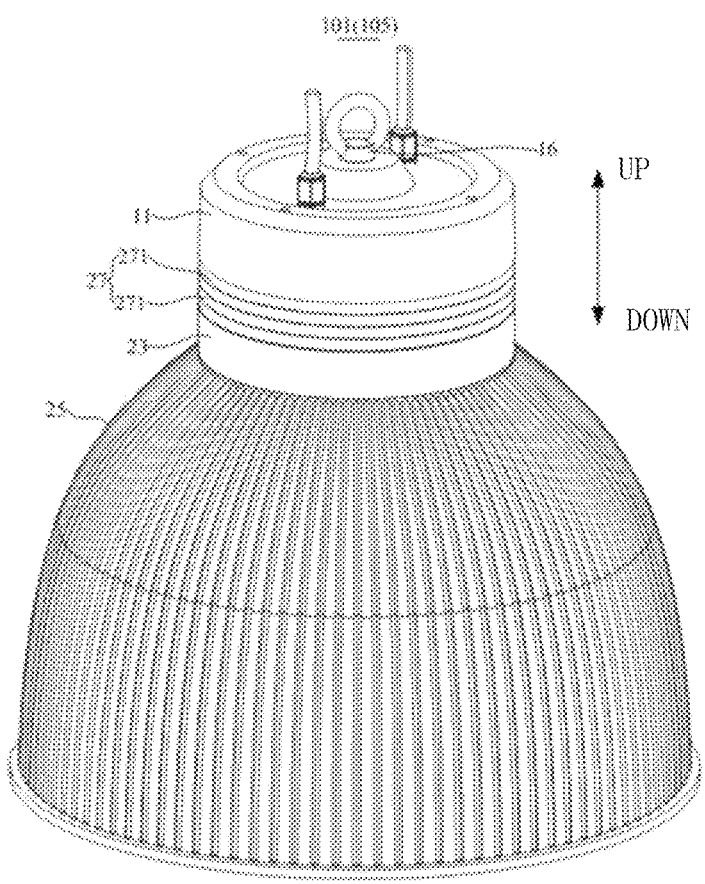
FIG. 9 is a schematic diagram showing the structure of one perspective of one embodiment of the ventilation-type UV mining lamp in the present disclosure.
Figure 10:
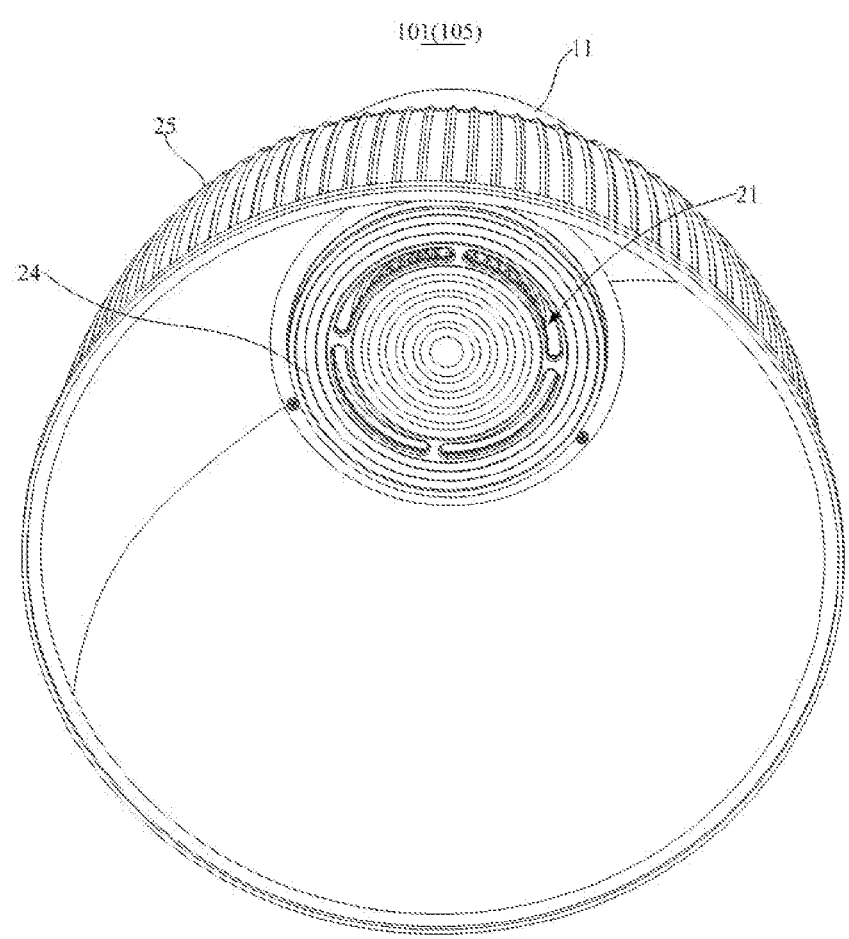
FIG. 10 is a schematic diagram showing the structure of another perspective of the ventilation-type UV mining lamp in FIG. 9.
Figure 11:
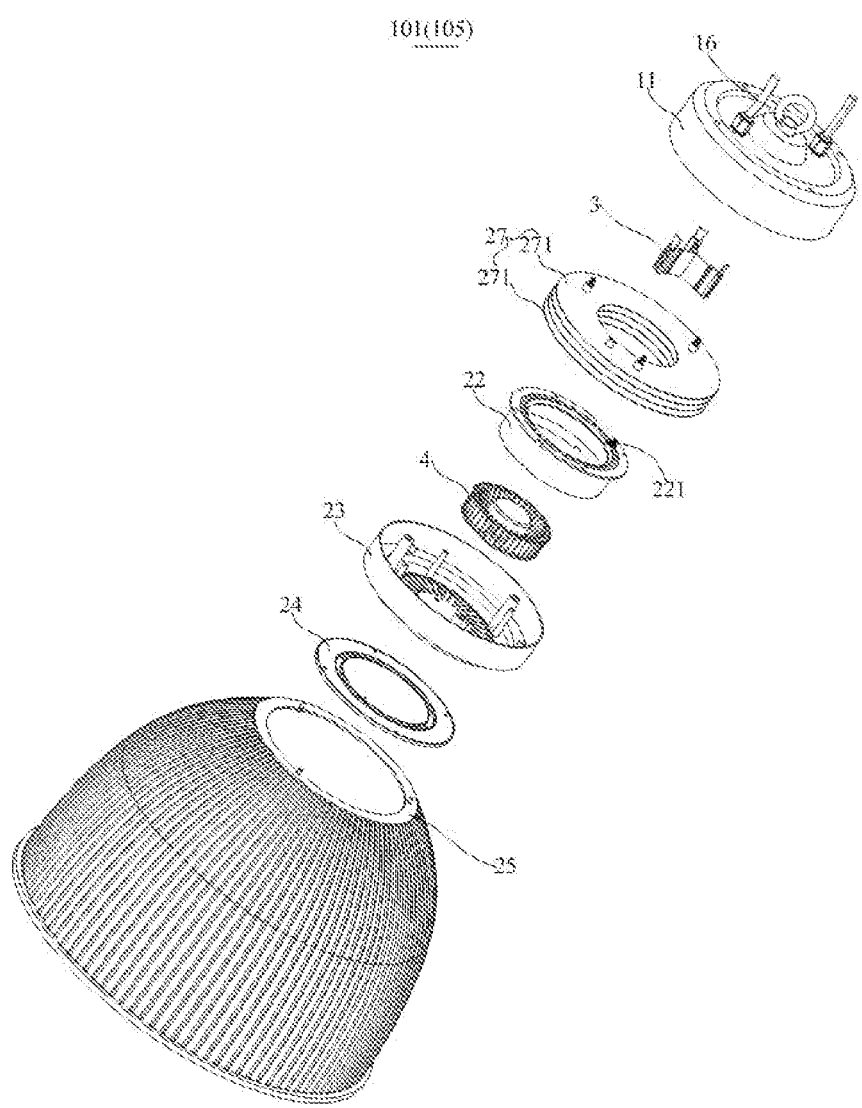
FIG. 11 is a schematic diagram showing the structure of one perspective of the explosion structure of ventilation-type UV mining lamp in FIG. 9.
Figure 12:
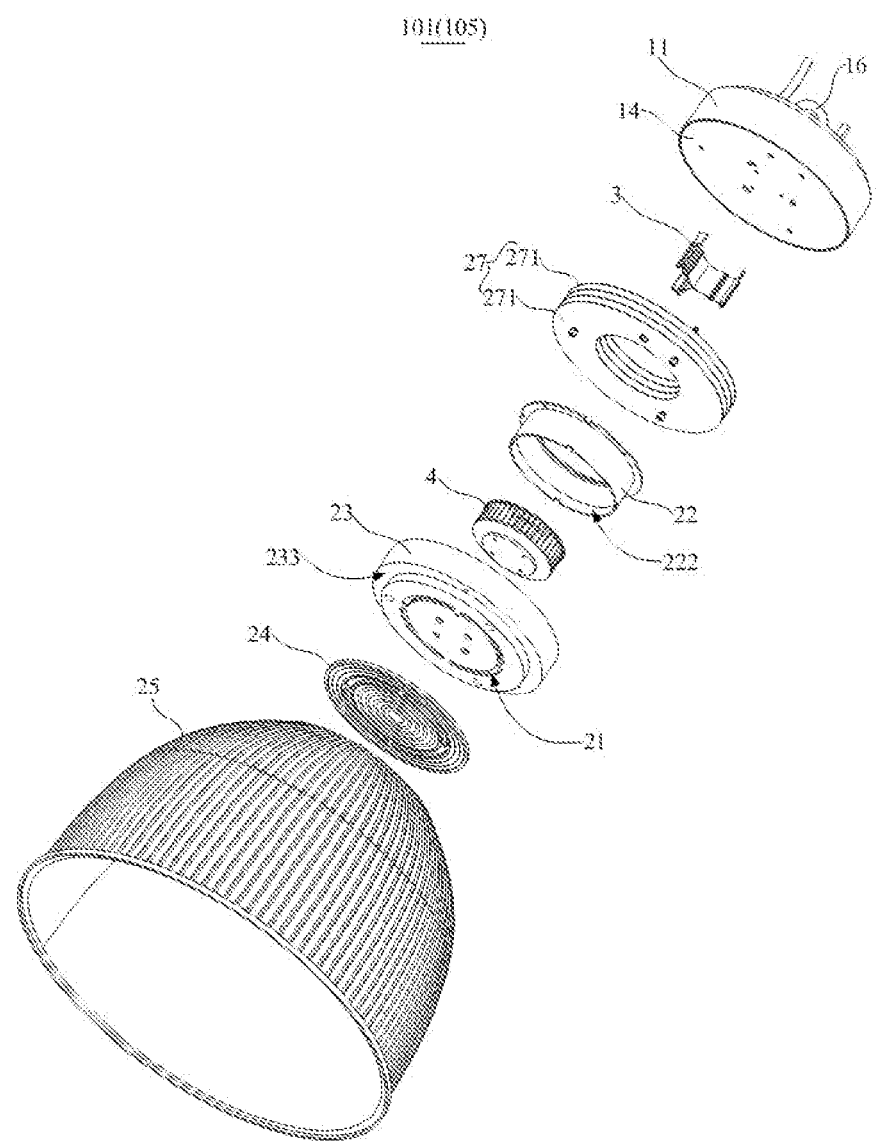
FIG. 12 is a schematic diagram showing the structure of another perspective of the explosion structure of ventilation-type UV mining lamp in FIG. 9.
Figure 13:
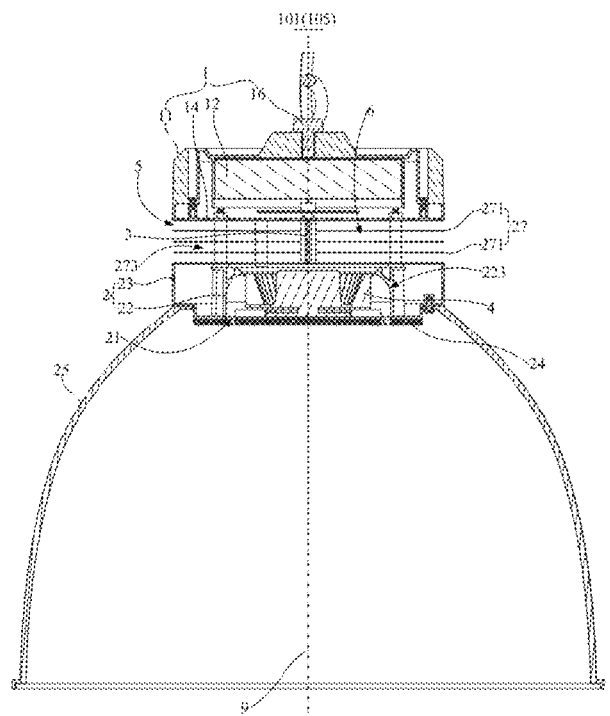
FIG. 13 is a diagrammatic cross section of ventilation-type UV mining lamp in FIG. 9.

According to FIGS. 6-8, in one embodiment of the present disclosure, light body 1 also comprises a control box 11, a driving power supply 12 and a dimmer switch 13. Wherein, the control box 11 can be used for accommodating driving power supply 12. In such a case, control box 11 is on the top of light body 1. Driving power supply 12 can supply power for UV module 3 to drive it, so that UV module 3 and other electric parts can work with stable power supply. Dimmer switch 13 can be used for regulating the color temperature or power of ventilation-type UV light 101. For example: dimmer switch 13 can comprise two opposite buckles 131, toggling part 133 and plugging hole 135; buckles 131 comprise an extension arm 132 and a stuck point 225; buckles 131 and plugging hole 135 are provided on one end away from toggling part 133; control box 11 is provided with sliding holes 114, two buckles 131 slide into sliding hole 114, dimmer switch 13 connects to control box 11 in a flexible way via two extension arms 132 and stuck points 225 at intervals; driving power supply 12 comprises a toggle switch 121 inserted into the plugging hole 135, and the corresponding gear of color temperature or power can be regulated by sliding the toggling part 133. In other embodiments, lights can be provided with two dimmer switches 13 for regulating color temperature and power respectively. Further, the inside of mounting space 6 can also be provided with a reflective board 61 via which the number of reflection of UV rays emitted by UV module 3 can be increased, so that the sterilization and disinfection efficiency of air inside mounting space 6 can be improved.

Further, when the above-mentioned ventilation-type UV light 101 is ventilation-type UV downlight 103, according to FIGS. 3-5, light body 1 also comprises a mounting subassembly 14 that can be provided at the bottom of control box 11, the bottom of this mounting subassembly 14 is provided with a groove 141 with a downward opening, the air guide structure 2 can be inserted into this groove 141 and enclose with mounting subassembly 141 to form a mounting space 6. In other embodiments, this mounting subassembly 14 can be of different structures and shapes, such as tablet shape or arc shape.

Ventilation-type UV downlight 103 is further described below:

According to FIG. 5, in one embodiment of the present disclosure, mounting subassembly 14 comprises a convex part 145 and lateral margin 147 provided on the periphery of convex part 145. Convex part 145 is provided with a groove 141 with a downward opening, air guide structure 2 and light body 1 enclose to form mounting space 6 and air inlet 5, and air inlet 5 is located on the lateral margin 147. The mounting position can be provided via the lateral margin 147, so that air guide structure 2 and mounting subassembly 14 can be connected conveniently. Specifically speaking, baseplate 23 of air guide structure 2 can be provided with a connecting column 231 corresponding to lateral margin 147, and light body 1 and air guide structure 2 are connected in a dismountable way via the connecting column 231 and corresponding fasteners 84 (e.g. screw). Additionally, to prevent external objects flow into mounting space 6 via air inlets 5, air inlets 5 are provided with a protective cover 51. Protective cover 51 can be provided in a loop shape and provided between the lateral margin 147 of mounting subassembly 14 and baseplate 23 of air guide structure 2.

According to FIGS. 4-5, in one embodiment of the present disclosure, a fixed surface 143 is formed on the inner sidewall of groove 141, and fixed surface 143 is provided in a plane shape, so that UV module 3 can be installed onto fixed surface 143 conveniently. Wherein, UV module 3 can connect the inner sidewall of mounting subassembly 14 in a dismountable way via screws or clamps. Additionally, the quantity of UV module 3 can be at least two, and at least two UV modules 3 are provided in mounting space 6 and distributed uniformly at intervals around center line of wind scooper 22 to further improve the sterilization and disinfection effect of air in mounting space 6.

According to FIGS. 6-7, in one embodiment of the present disclosure, control box 11 comprises the first accommodating groove 111 with a downward opening and the second accommodating groove 113 with a downward opening, and driving power supply 12 is provided inside the first accommodating groove 111. Light body 1 can also comprise a cover plate 15 that covers the second accommodating groove 113 in a dismountable way, the second accommodating groove 113 can be used for accommodating lead, so that lead and driving power supply 12 can be accommodated separately in control box 11 to improve the installation convenience and safety. In addition, the second accommodating groove 113 can be provided with one or several horizontal standby cord holes 117, via which the external wire and wiring tube can access the second accommodating groove 113, providing a horizontal wiring mode. Control box 11 can also be provided with a cord hole 115 that can access the first accommodating groove 111, the second accommodating groove 113 and the top wall of the first accommodating groove 111; Driving power supply 12 comprises power cable 122 that passes through the cord hole 115; After opening cover plate 15, without taking power cable 122 out of the cord hole, power cable 122 can pass through the first accommodating groove 111 and access the outside of the top wall of the first accommodating groove 111, can also pass through the first accommodating groove 111 and access the second accommodating groove 113 to realize fast switch of the wiring mode. In such a way, there is no need to set two wiring ports at the power input end of driving power supply 12.

Further, when the specific type of the aforethe ventilation-type UV light 101 is ventilation-type UV mining lamp 105, according to FIGS. 9-13, light body also comprises a fixed structure 16 provided on the top of control box 11. Such a fixed structure 16 can be a swinging ring or hook that can improve the installation convenience of ventilation-type UV mining lamp 105. In addition, light body 1 can also comprise a mounting subassembly 14, control box 11 is provided on the top of mounting subassembly 14 or covers mounting subassembly 14, so that control box 11 and mounting subassembly 14 can enclose to form a space for accommodating driving power supply 12.

Ventilation-type UV mining lamp 105 is further described below:

According to FIGS. 10-13, in one embodiment of the present disclosure, the bottom of air guide structure 2 is provided with a bottom lighting module 24, at least one part of bottom lighting module 24 is surrounded by air outlet 21, three projections of bottom port 222, bottom lighting module 24 surrounded by air outlet 21 and top port 221 on the horizontal plane are provided in the descending order. Bottom lighting module 24 can provide lighting for the environment where ventilation-type UV mining lamp is located, so as to improve the service performance of ventilation-type UV mining lamp 105.

In one embodiment of the present disclosure, air guide structure 2 can also comprise a baseplate 23 and a bottom lighting module 24, bottom lighting module 24 is provided on baseplate 23, and baseplate 23 can serve as a radiator of bottom lighting module 24. Further, the bottom periphery of baseplate 23 is provided with a step structure 233 that surrounds bottom lighting module 24. In such a case, according to FIGS. 12-13, air guide structure 2 can also comprise a housing 25 provided on step structure 233, to improve the lighting quality of bottom lighting module 24 via housing 25. Or, according to FIGS. 17-18, air guide structure 2 can also comprise a mounting loop 26 installed onto step structure 233 to protect the luminous surface of bottom lighting module 24 via mounting loop 26. To achieve better option and use, housing 25 or mounting loop 26 can connect to step structure 233 in a dismountable way.

According to FIGS. 9-13, in one embodiment of the present disclosure, air guide structure 2 can also comprise grating subassembly 27 provided on the top of air guide structure 2, grating subassembly 27 comprises several annular partition boards 271 provided at intervals, a light emitting groove 273 is formed between adjacent partition boards 271, UV rays emitted from UV module 3 go out of the light body 1 via light emitting groove 273, and light emitting grooves 273 constitutes air inlets 5. In such a case, grating subassembly 27 can protect UV module 3 in mounting space 6 to reduce the possibility of damage arising from other objects, so that ventilation-type UV mining lamp 105 can have the strengths of both upper-layer horizontal emission UV light and built-in UV lights.

Figure 14:
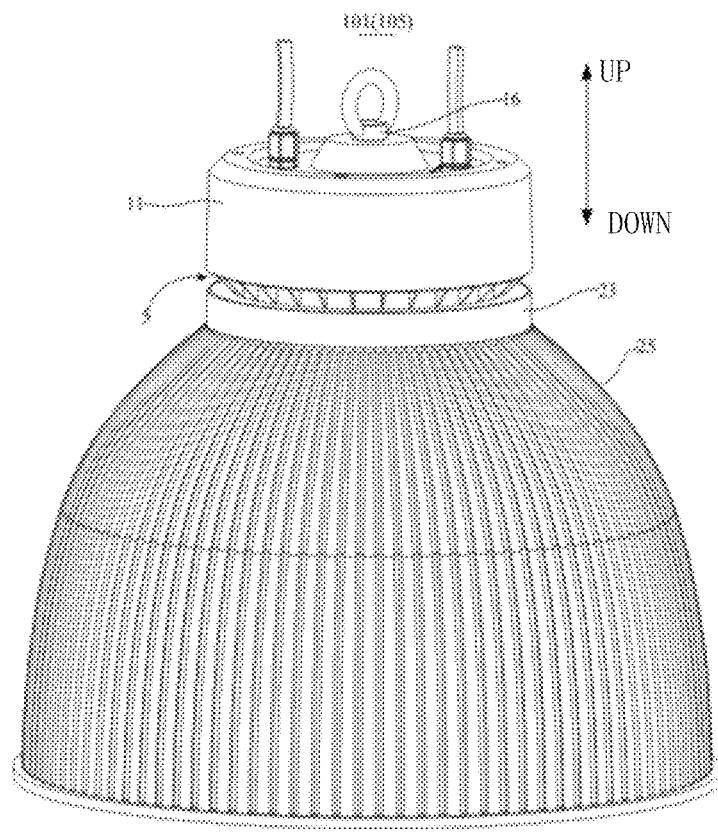
FIG. 14 is a schematic diagram showing the structure of one perspective of another embodiment of the new-type ventilation-type UV mining lamp in the present disclosure.
Figure 15:
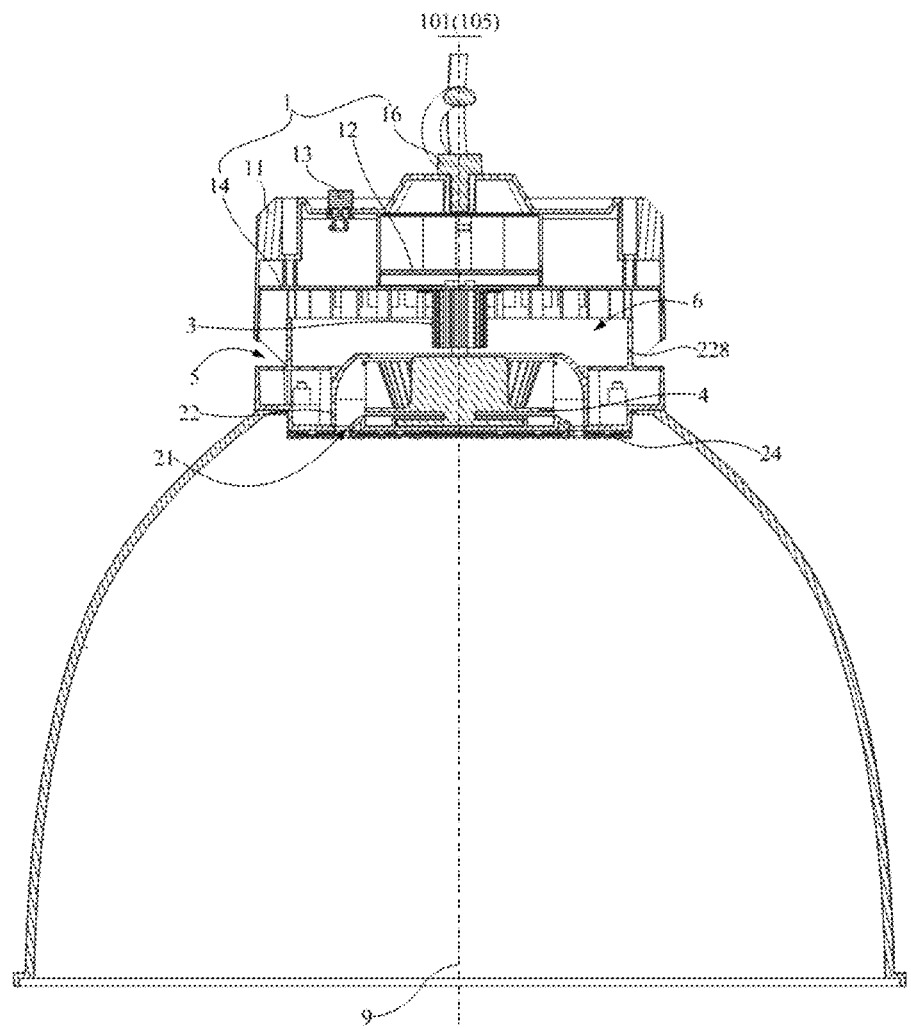
FIG. 15 is a diagrammatic cross section of ventilation-type UV mining lamp in FIG. 14.
Figure 16:
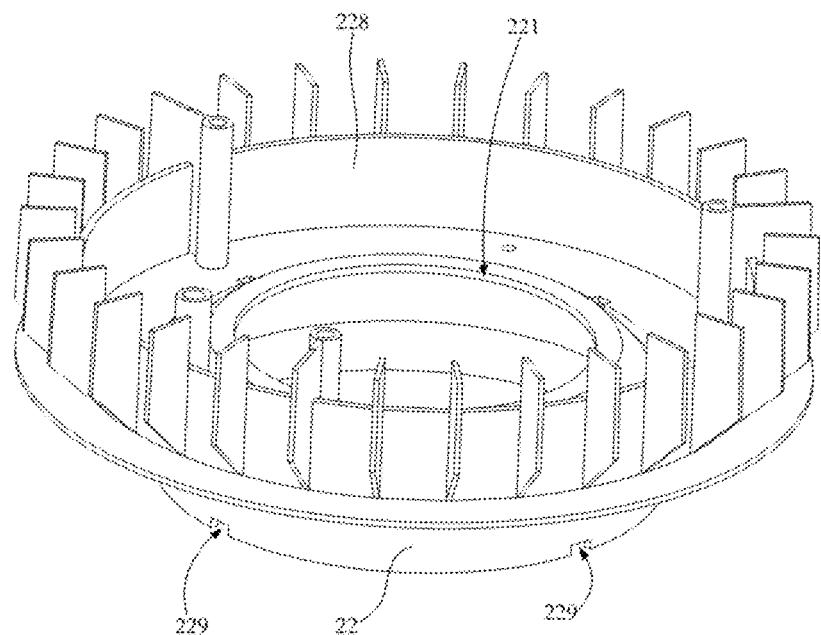
FIG. 16 is a schematic diagram showing the structure of the wind scooper of ventilation-type UV mining lamp in FIG. 14.
Figure 17:
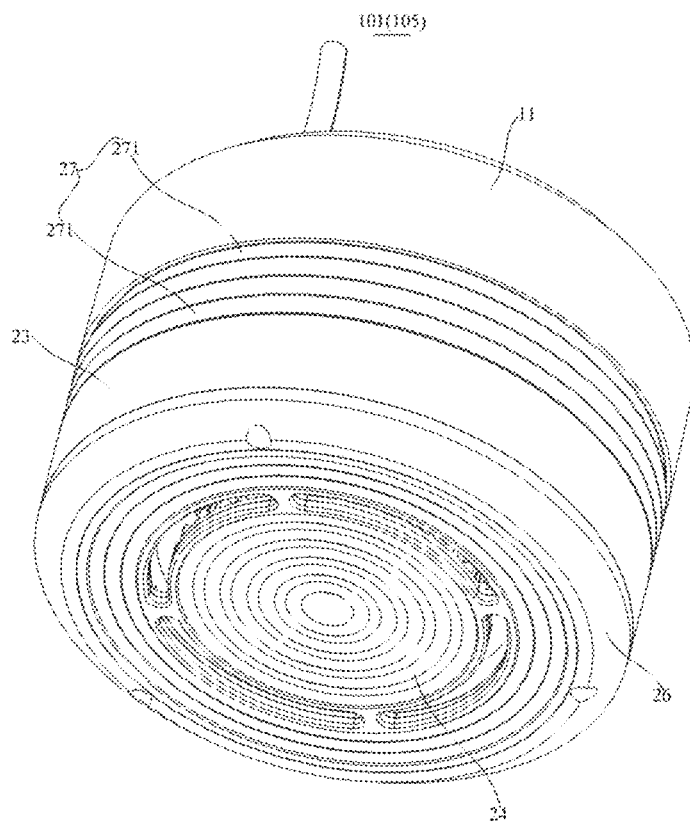
FIG. 17 is a schematic diagram showing the structure of one perspective of yet another embodiment of the new-type ventilation-type UV mining lamp in the present disclosure.
Figure 18:
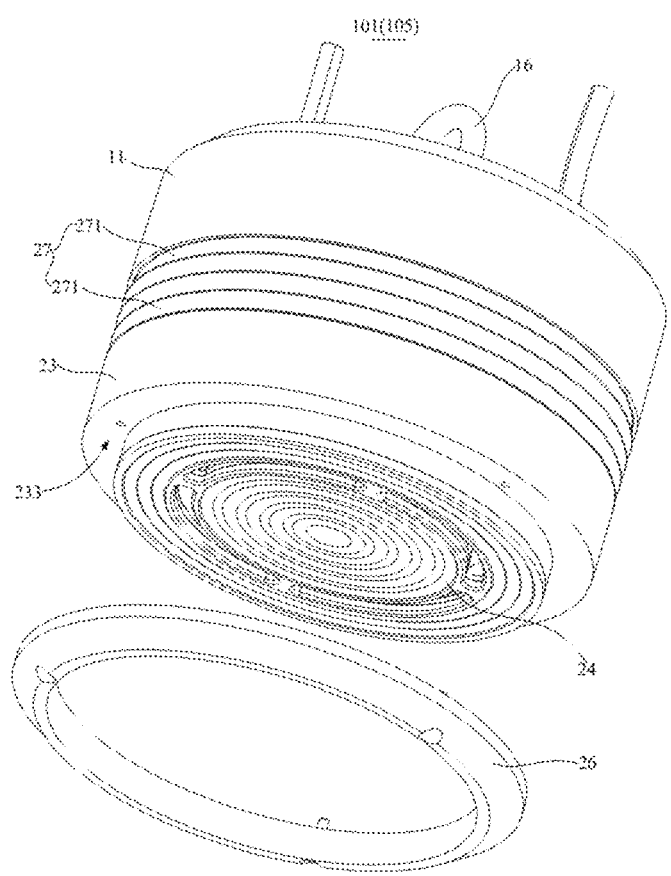
FIG. 18 is a schematic diagram showing the explosion structure of ventilation-type UV mining lamp in FIG. 17.
Figure 19:
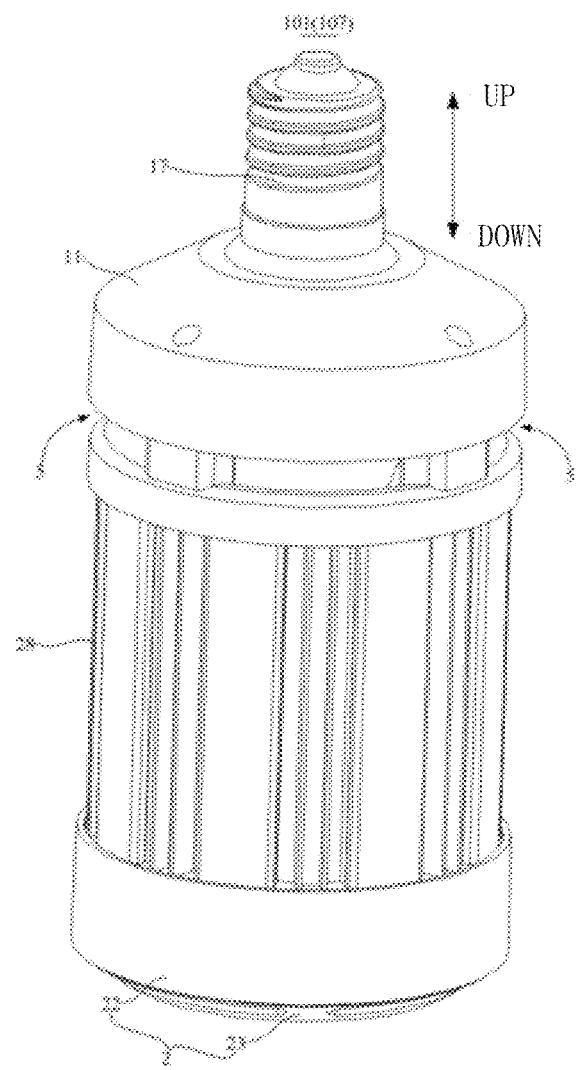
FIG. 19 is a schematic diagram showing the structure of one perspective of one embodiment of the new-type ventilation-type UV corn lamp in the present disclosure.
Figure 20:
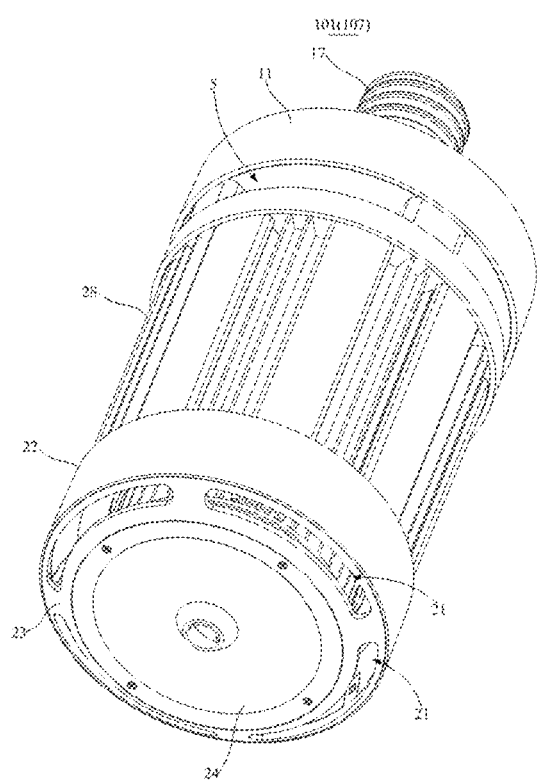
FIG. 20 is a schematic diagram showing the structure of another perspective of the ventilation-type UV corn lamp in FIG. 19.

According to FIGS. 14-16, in one embodiment of the present disclosure, wind scooper 22 is provided with a circle of enclosing edge 228 corresponding to air inlets 5, control box 11 can be a structure with a downward opening, control box 11 covers mounting subassembly 14, and the sidewall of control box 11 extends downward to the place lower than the top of the enclosing edge 228. In such a case, sidewall of control box 11 and enclosing edge 228 of wind scooper 22 can also protect UV module 3 inside mounting space 6.

Further, the periphery bottom of wind scooper 22 is provided with several the first ventilation holes 229, so that fan 4 can accelerate air flow outside wind scooper 22 via the first ventilation holes 229, to improve the heat radiation of baseplate 23.

Further, when the aforethe ventilation-type UV light 101 is ventilation-type UV corn lamp 107, according to FIGS. 19-23, light body 1 can also comprise a light cap 17 that can be E27 light cap 17, B22 light cap 17 or other fixed light caps 17, to facilitate installation of ventilation-type UV corn lamp 107. Air guide structure 2 can also comprise a lateral lighting module 28 that can be a hollow structure and provided on the top of air guide structure 2 and surround mounting space 6, so that lateral lighting module 28 can illuminate towards the periphery of ventilation-type UV corn lamp 107. Wherein, lateral lighting module 28 can also comprise a hollow radiator 281 and a reflective board 61, radiator 28 comprises a center hole 283 in the up-down direction, the circumferential wall of center hole 283 is provided with a clamping slot 285 in the up-down direction, clamping slot 285 is in the T shape, and reflective board 61 is inserted into clamping slot 285. Or, lateral lighting module 28 comprises a hollow radiator 281, radiator 281 comprises a center hole 283 in the up-down direction, the hole wall of center hole 283 is provided with a circle of air inlets that connect center hole 283 and the peripheral space of radiator 281. In addition, the air inlet 5 of ventilation-type UV corn lamp 107 can be provided on the top, circumferential wall or bottom of radiator 281 in a surrounding way. According to FIGS. 24-25, the lateral side of radiator 281 can comprise several strip illumination areas in the up-down direction, each strip illumination area comprises one the second light panel 243, lamp bead 245 provided on the second light panel 243 and housing 25 that covers the second light panel 243.

Ventilation-type UV corn lamp 107 is further described below:

According to FIGS. 20-23, in one embodiment of the present disclosure, the bottom of air guide structure 2 is provided with a bottom lighting module 24, at least one part of bottom lighting module 24 is surrounded by air outlet 21, three projections of bottom port 222, bottom lighting module 24 surrounded by air outlet 21 and top port 221 on the horizontal plane are provided in the descending order. In such a case, baseplate 23 can be one part of bottom lighting module 24.

Figure 21:
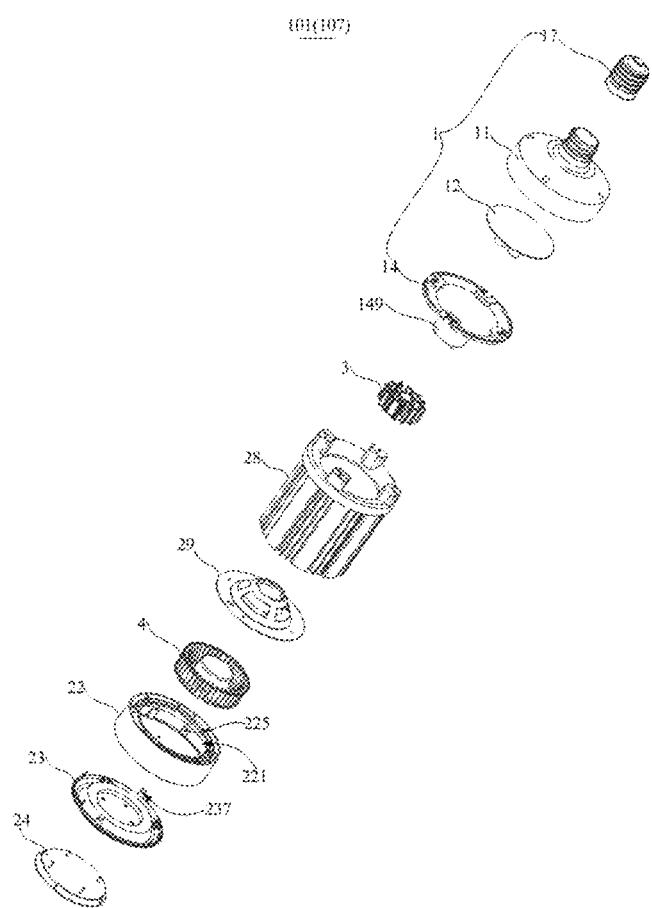
FIG. 21 is a schematic diagram showing the structure of one perspective of the explosion structure diagram of ventilation-type UV corn lamp in FIG. 19.
Figure 22:
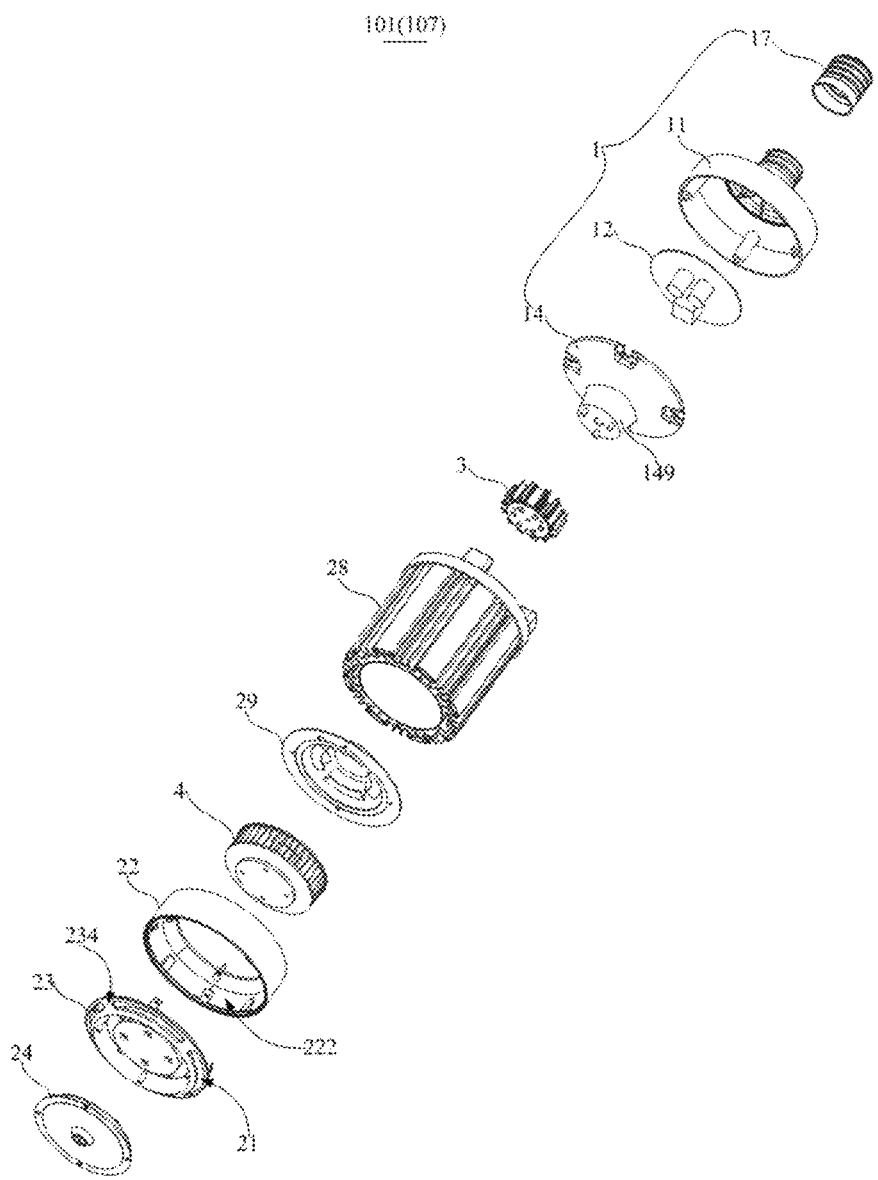
FIG. 22 is a schematic diagram showing the structure of another perspective of the explosion structure diagram of ventilation-type UV corn lamp in FIG. 19.
Figure 23:
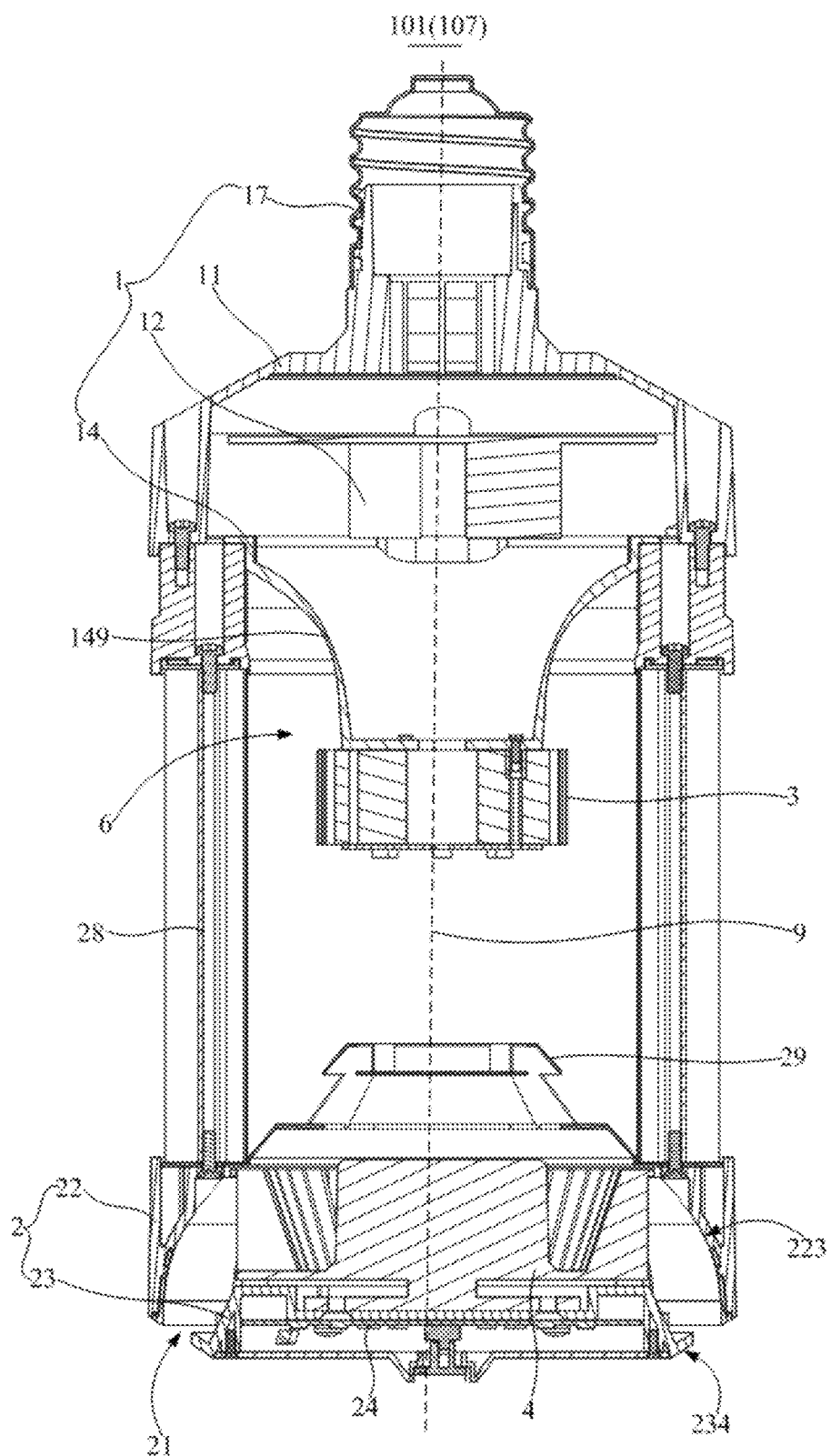
FIG. 23 is a diagrammatic cross section of ventilation-type UV corn lamp in FIG. 19.
Figure 24:
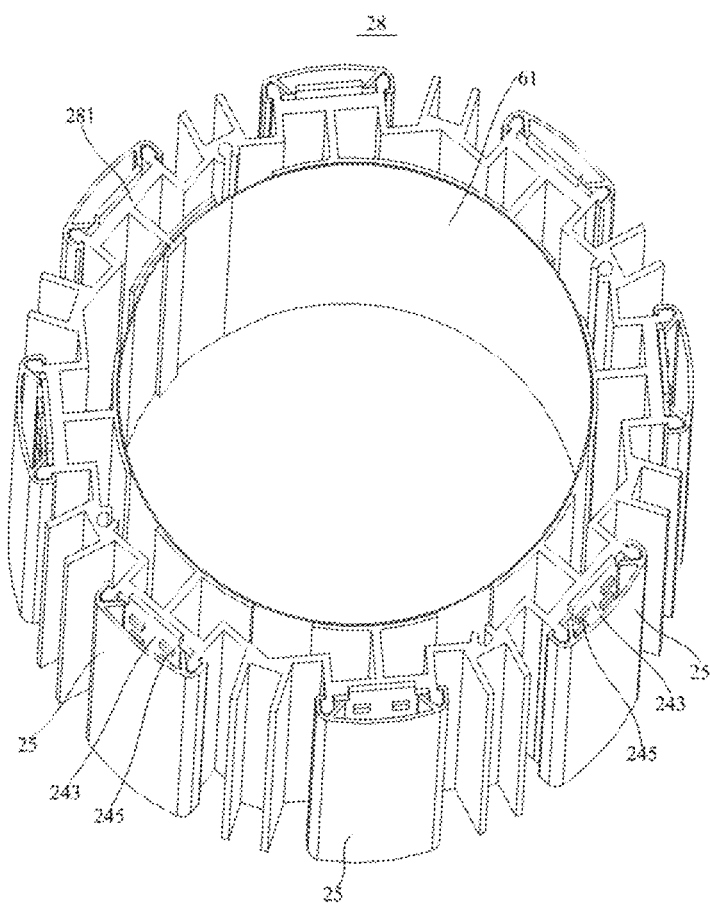
FIG. 24 is a schematic diagram showing the local structure of the UV module of ventilation-type UV corn lamp in FIG. 19.
Figure 25:
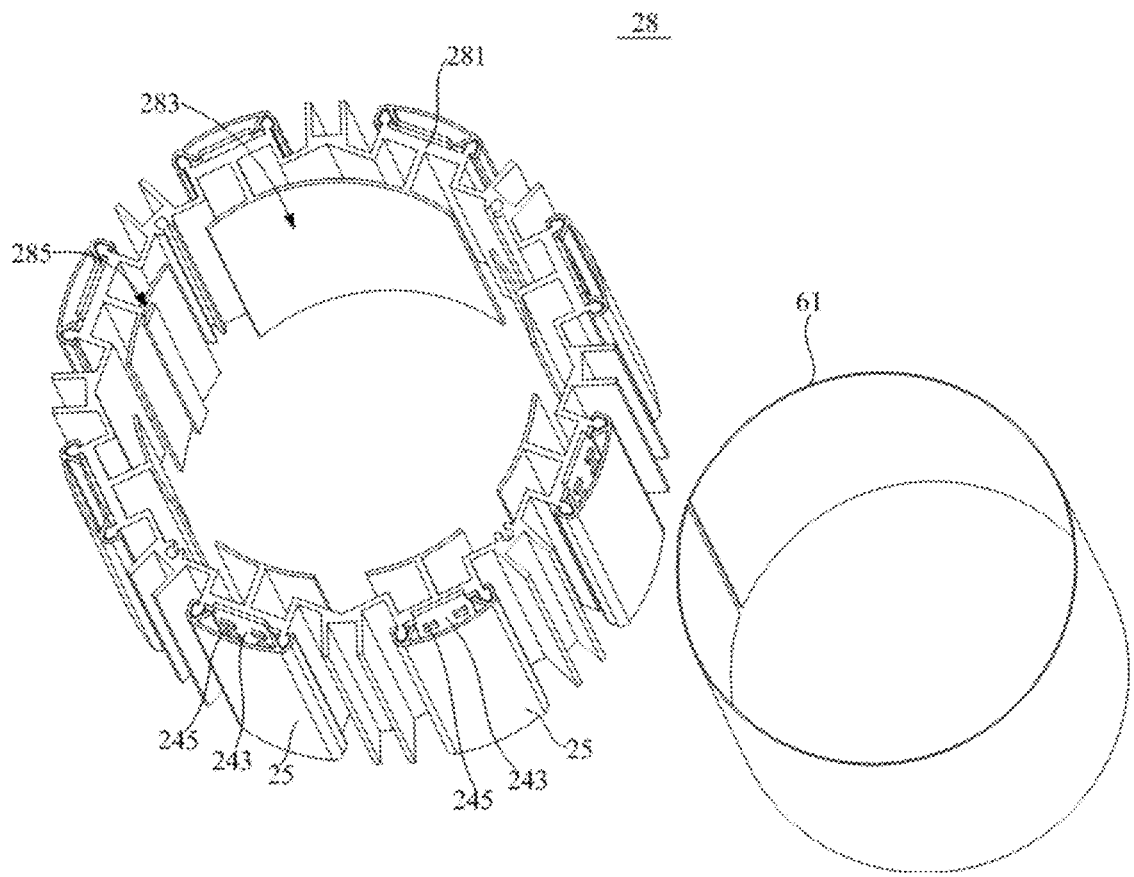
FIG. 25 is a schematic diagram showing the explosion structure of UV module in FIG. 24.
Figure 26:
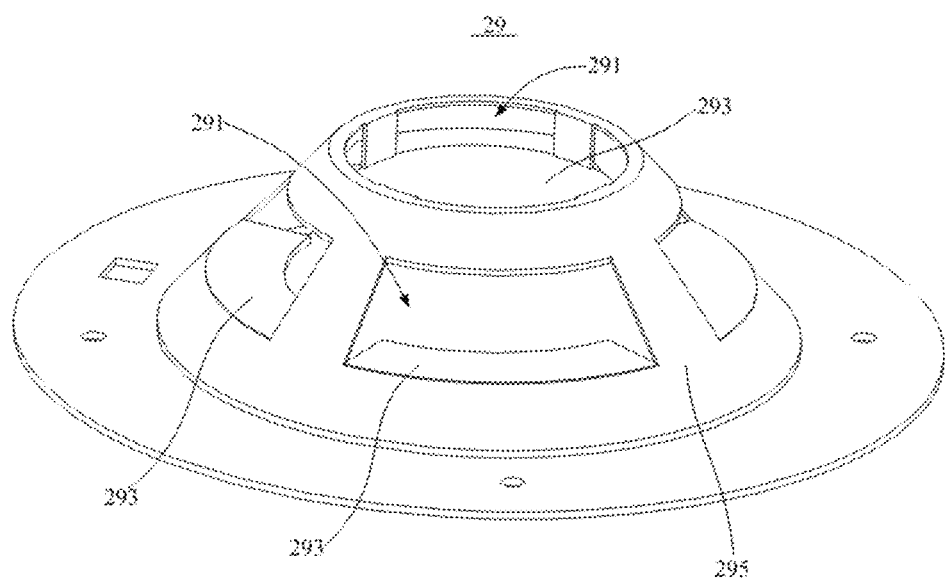
FIG. 26 is a schematic diagram showing the structure of the light shield of ventilation-type UV corn lamp in FIG. 19.
Figure 27:
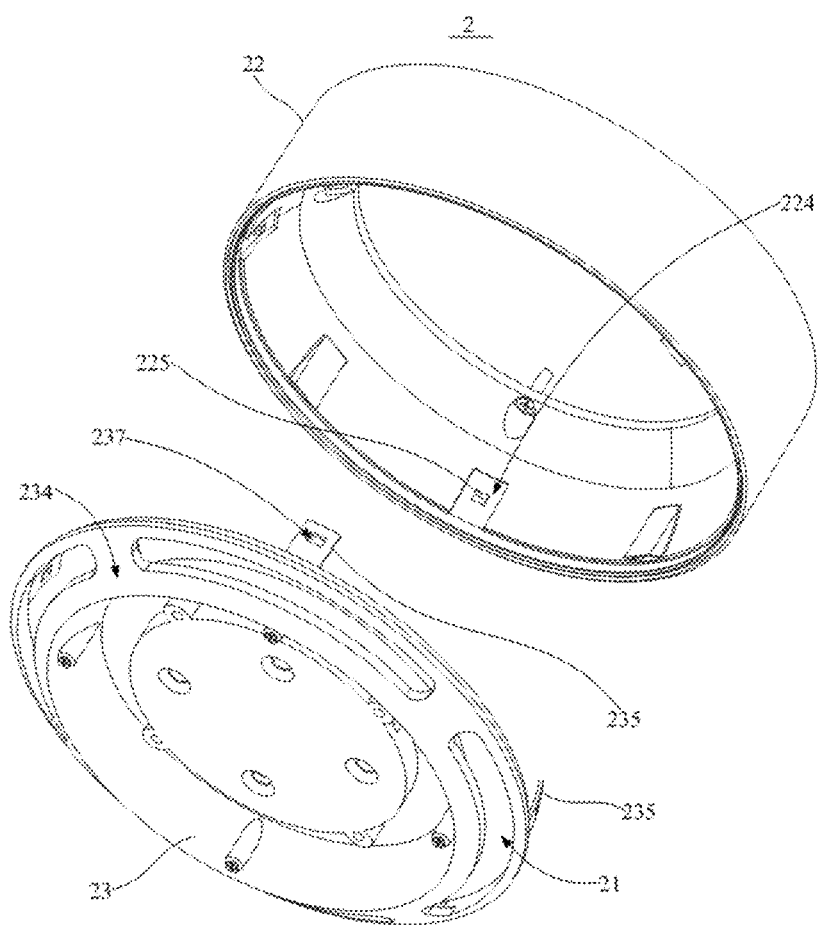
FIG. 27 is a schematic diagram showing the structure of the wind scooper of ventilation-type UV corn lamp in FIG. 19.
Figure 28:
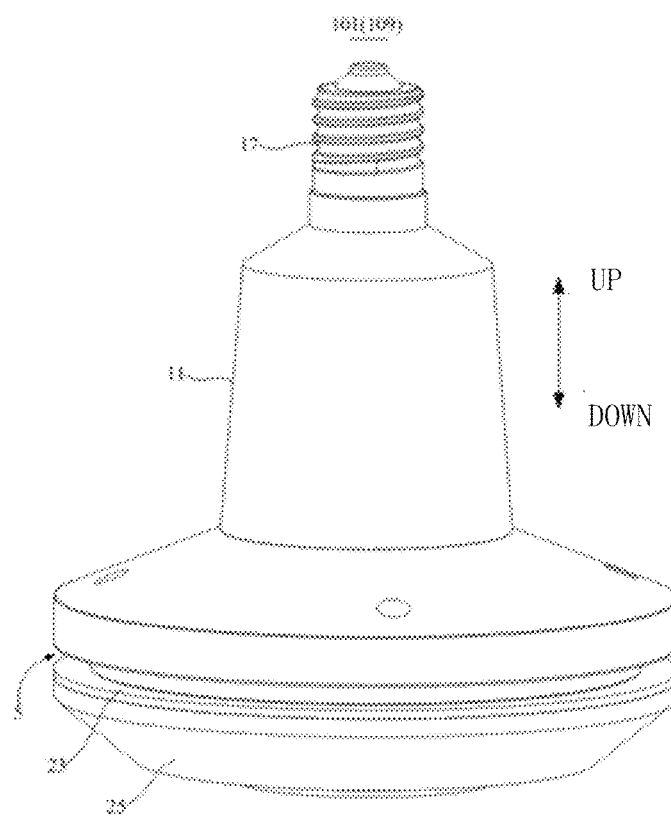
FIG. 28 is a schematic diagram showing the structure of one perspective of one embodiment of the new-type ventilation-type UV bulb in the present disclosure.

According to FIGS. 21-23, in one embodiment of the present disclosure, light body 1 can also comprise a mounting subassembly 14 provided at the bottom of light body 1, and control box 11 is provided on the top of mounting subassembly 14 or covers mounting subassembly 14. Wherein, mounting subassembly 14 can comprise a tapered structure 149 that extends downward to the internal space of lateral lighting module 28, and UV module 3 is provided at the bottom of tapered structure 149. Through setting the tapered structure 149, there will be a relatively big space for air flow outside the tapered structure 149, so that the liquidity of air can be guaranteed, and UV module 3 is provided in the position nearby the center of mounting space 6 to improve the utilization ratio of UV rays reflected by UV module 3.

According to FIGS. 23-26, in one embodiment of the present disclosure, air guide structure 2 also comprises a light shield 29 between UV module 3 and top port 221, light shield 29 comprises the second ventilation hole 291 and protective plate 293, the second ventilation hole 291 accesses mounting space 6 and top port 221, protective plate 293 is used for shielding UV rays, and the projection of protective plate 293 on the plane covers the projection of the second ventilation hole 291 on the plane. In such a case, protective plate 293 can shield vertically downward UV rays. Further, light shield 29 comprises an upward convex structure 295; There are several second ventilation holes 291 respectively provided on the top and sidewall of convex structure 295, and protective plate 293 is provided horizontally, to reflect the light emitted by bottom lighting module 24 and improve the lighting effect of bottom lighting module 24.

According to FIGS. 20-23, in one embodiment of the present disclosure, the periphery of wind scooper 22 is provided in a column shape, the peripheral surface of baseplate 23 includes inclined surfaces 234, air outlets 21 are provided on inclined surfaces 234, and the peripheral surface of baseplate 23 is aligned with that of wind scooper 22. Such setting makes the structure of ventilation-type UV corn lamp 107 more compacted, and air can flow out obliquely downward. Further, according to FIG. 27, air guiding plane 223 of wind scooper 22 is provided with several mounting groove 224, the inside of mounting groove 224 is provided with stuck point 225, baseplate 23 is provided with several mounting columns 225 corresponding mounting groove 224, mounting columns 235 are provided with clamping holes 237, stuck points 225 are installed inside clamping holes 237, so that wind scooper 22 and baseplate 23 can be fixed in the clamping way conveniently.

Further, when the aforethe ventilation-type UV light 101 is ventilation-type UV bulb 109, according to FIGS. 28-31, light body 1 can also comprise a light cap 17 that can be E27 light cap 17, B22 light cap 17 or other fixed light caps 17, to facilitate installation of ventilation-type UV bulb. Air guide structure 2 can also comprise a bottom lighting module 24 via which the lighting performance is improved.

Figure 29:
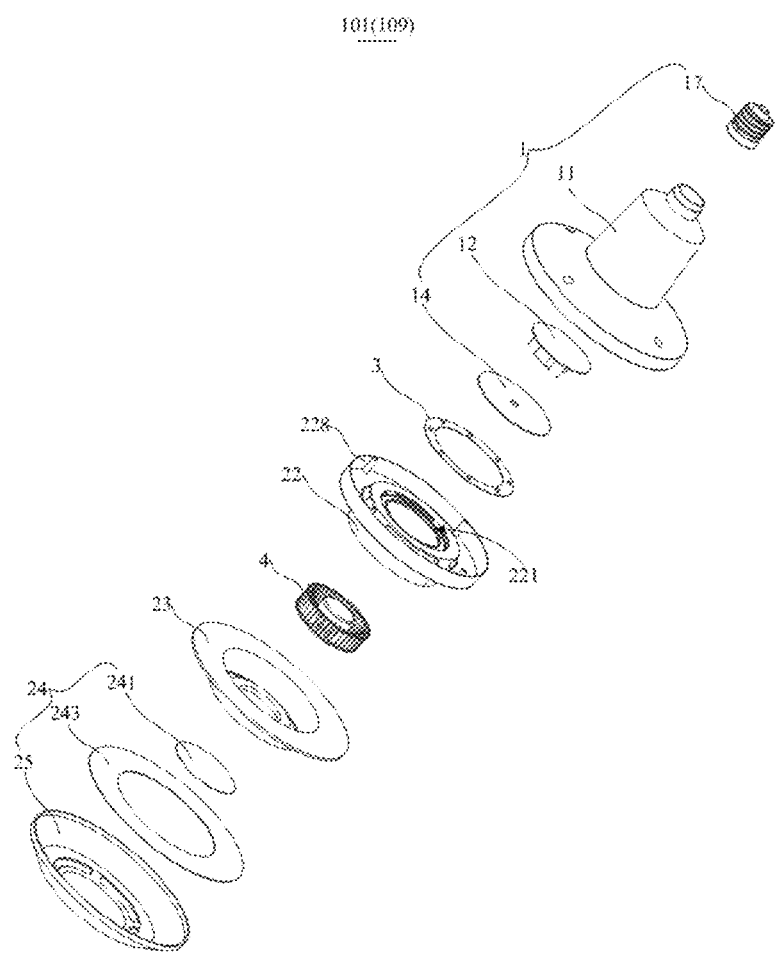
FIG. 29 is a schematic diagram showing the structure of one perspective of the explosion structure of ventilation-type UV bulb in FIG. 28.
Figure 30:
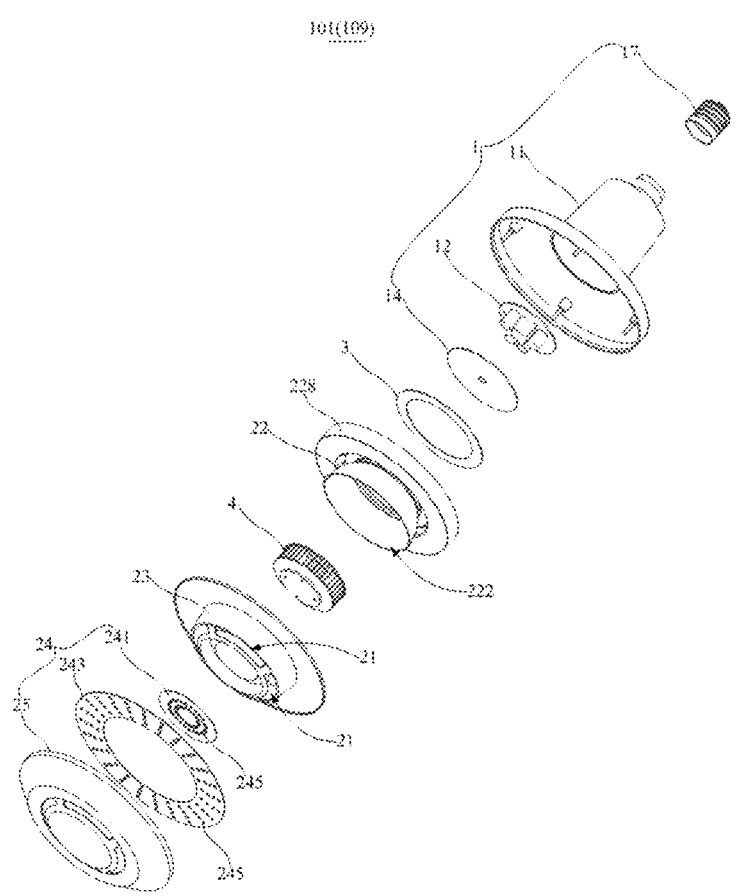
FIG. 30 is a schematic diagram showing the structure of another perspective of the explosion structure of ventilation-type UV bulb in FIG. 28.
Figure 31:
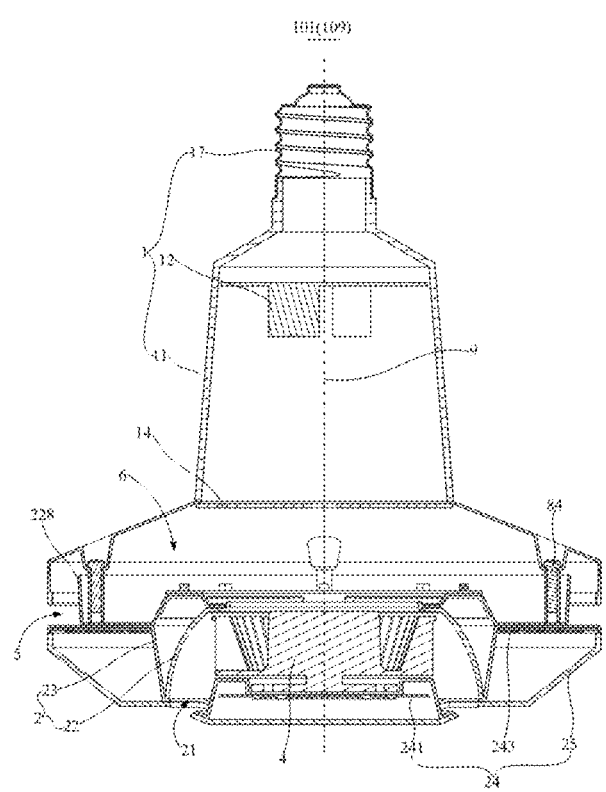
FIG. 31 is one cross section schematic of ventilation-type UV bulb in FIG. 28.
Figure 32:
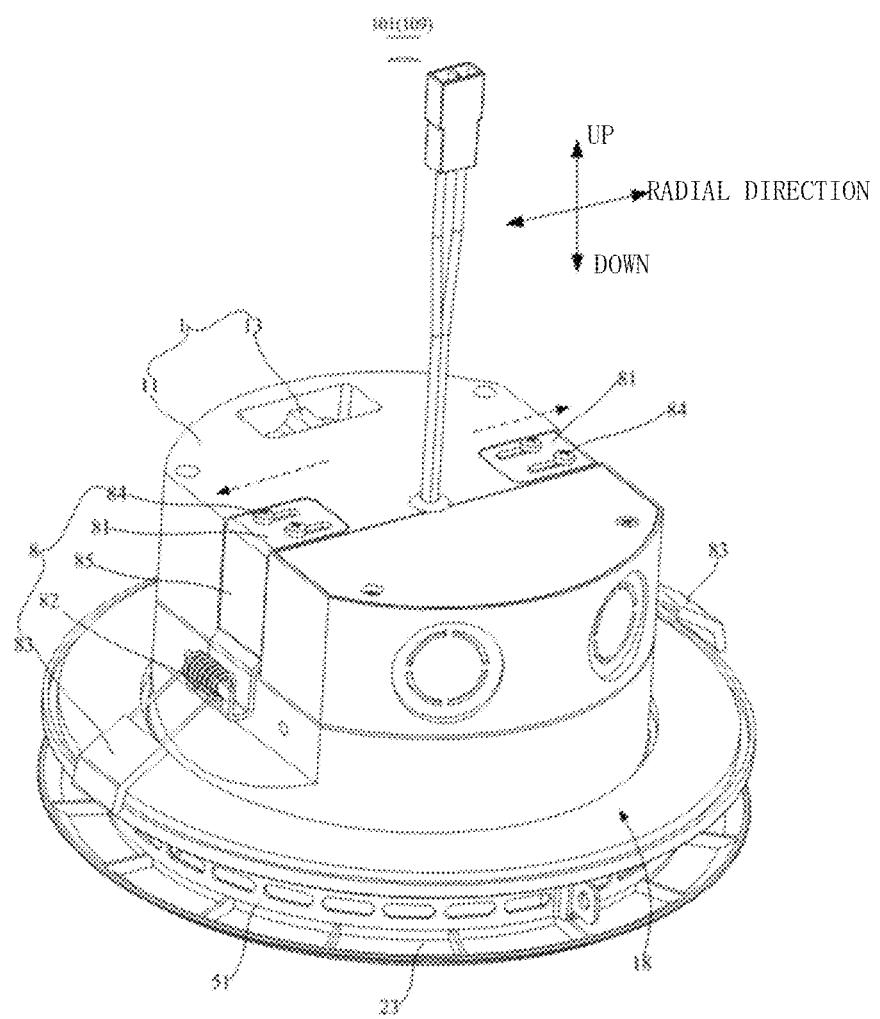
FIG. 32 is a schematic diagram showing the structure of an embodiment of a new-type downlight of the present disclosure.

Ventilation-type UV bulb is further described below:

According to FIGS. 29-31, in one embodiment of the present disclosure, at least one part of bottom lighting module 24 is surrounded by air outlet 21, baseplate 23 is one part of bottom lighting module 24, and three projections of bottom port 222, bottom lighting module 24 surrounded by air outlet 21 and top port 221 on the horizontal plane are provided in the descending order. Wherein, bottom lighting module 24 can comprise the first light panel 241, the second light panel 243 and housing 25. The first light panel 241 and the second light panel 243 are provided on the lower surface of baseplate 23, and the first light panel 241 and the second light panel 243 are provided with luminous lamp beads 245; Baseplate 23 and housing 25 are provided with air outlets 21 corresponding bottom port 222, air outlets 21 surround the first light panel 241, and the second light panel 243 surrounds air outlets 21; Housing 25 covers the first light panel 241 and the second light panel 243 and connects to baseplate 23 in a fixed way. The mounting height of the second light panel 243 can be higher than the first light panel 241, so that it can be installed more compactly, and the overall volume of ventilation-type UV bulb can be reduced.

According to FIG. 31, in one embodiment of the present disclosure, wind scooper 22 is provided with a circle of enclosing edge 228 corresponding to air inlets 5, light body 1 can comprise a mounting subassembly 14 provided at the bottom of light body 1; control box 11 is a structure with a downward opening, control box 11 covers mounting subassembly 14, and the sidewall of control box 11 extends to the position lower than the top of enclosing edge 228. In such a case, enclosing edge 228 and sidewall of control box 11 can isolate UV module 3 inside mounting space 6, preventing emission of UV rays from UV module 3 out of the light.

In such a case, UV module 3 can be provided inside wind scooper 22 and provided in a circular shape around the top port 221 of wind scooper 22.

Figure 33:
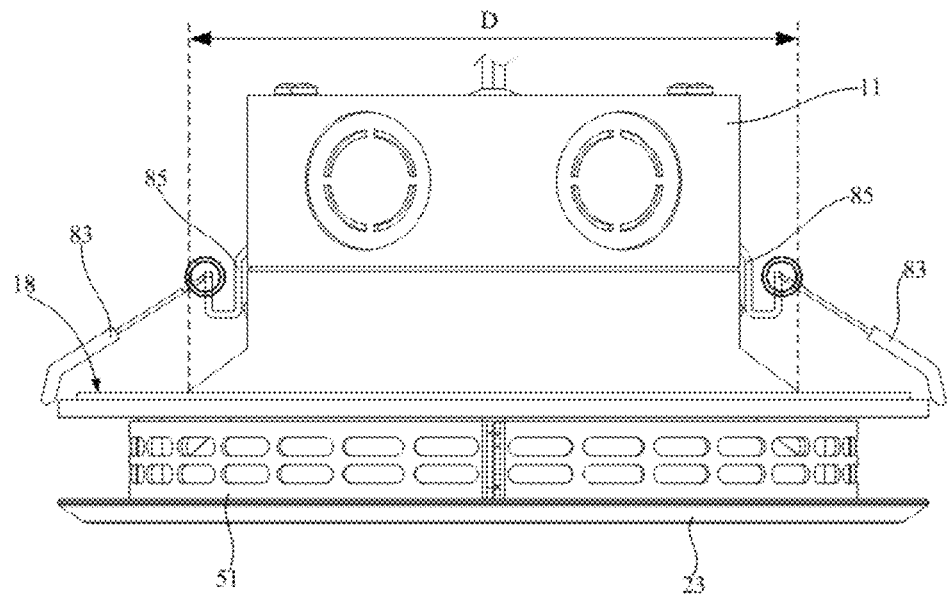
FIG. 33 is a schematic diagram showing the structure of one perspective of the downlight in FIG. 32.
Figure 34:
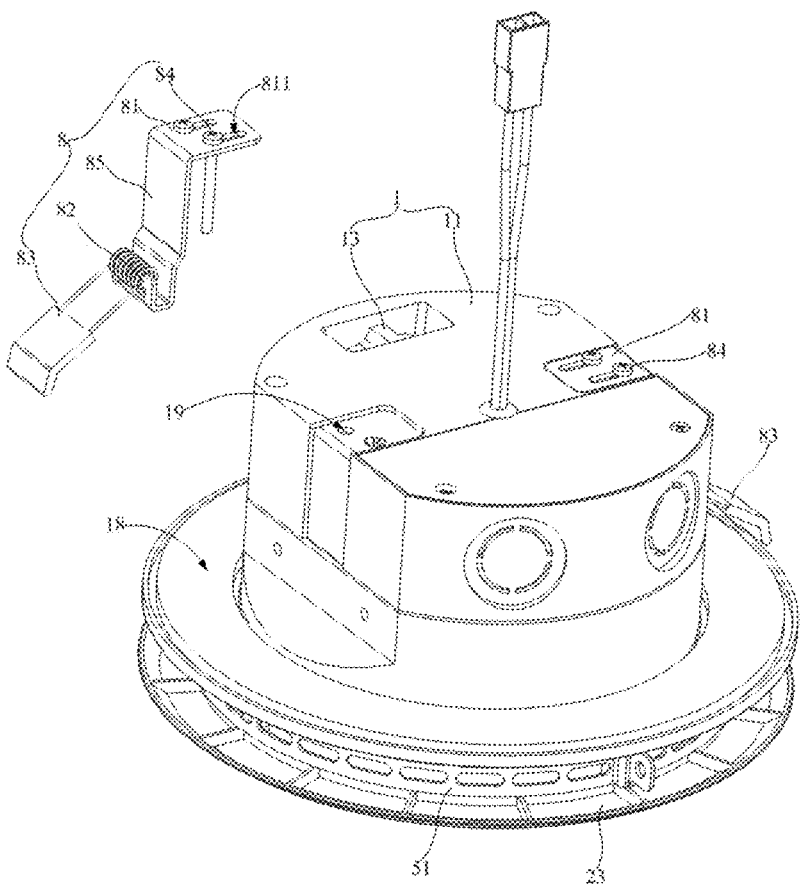
FIG. 34 is a schematic diagram showing the explosion structure of the light body and mounting subassemblies of the downlight in FIG. 32.
Figure 35:
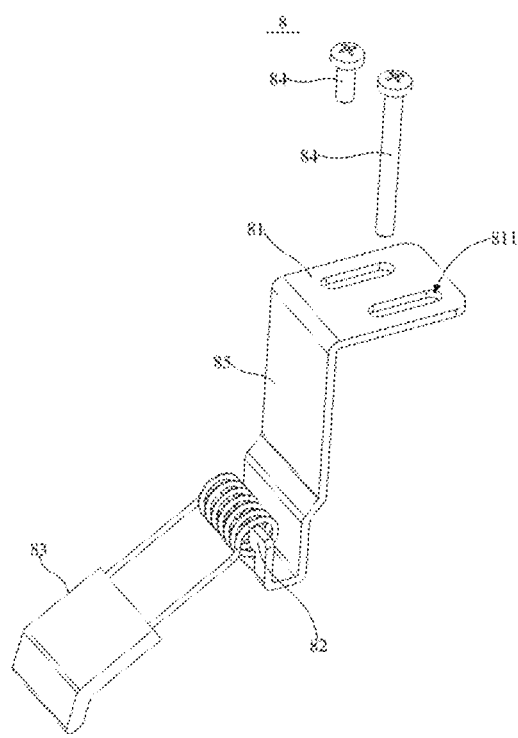
FIG. 35 is a schematic diagram showing the structure of the mounting subassemblies of the downlight in FIG. 32.

Further, different specifications of downlights are provided with different mounting holes, the opening size (D in FIG. 33 is the opening size of the downlight) of downlights is fixed. For example, 4 inches of downlight can only be installed in a 4 inches of mounting hole that passes through the upper surface and lower surface of external bearing part. The present disclosure invention also provides a structure that can regulate the opening size of downlights, which enables that the same downlight (the specific type can be the above-mentioned ventilation-type UV downlight 103) can be installed in several dimensions of mounting holes. Specifically speaking, mounting subassemblies 8 are designed into independent subassemblies that can connect to light body 1 of the downlight in a dismountable way. In other words, downlight comprises light body 1 and at least two mounting subassemblies 8. Light boy 1 comprises mounting surface 18 against the lower surface of the bearing part.

According to FIGS. 32-39, mounting subassemblies 8 comprise a fixed plate 81, engaging lugs 82 and clamping pieces 83, the fixed plate 81 is provided on the surface of the top of the light body horizontally (or the radial direction as shown in the FIG.) in a slidable way and can be located for fixing corresponding to the light body 1, the engaging lugs 82 and the fixed plates 81 are directly or indirectly connected, and the clamping pieces 83 are elastic parts installed on the engaging lugs 82; when downlight is installed in the mounting hole, clamping piece 83 can be against the upper surface of the bearing part, to install the downlight onto the bearing part in a fixed way. In such a case, fixed plate 81 can slide corresponding to light body 1, so fixed plate 81 in at least two mounting subassemblies 8 can be driven to different positions, that is, the distance between at least two mounting subassemblies 8 can be regulated, so that the downlight can be installed in different sizes of mounting holes. In different embodiments, clamping piece 83 can be a spring, shrapnel or other clamping structures, and engaging lug 82 can also be other structures that can fix clamping piece 83.

In one embodiment of the present disclosure, fixed plate 81 is provided with regulation holes 811 that are provided in the slide direction of fixed plate 81, mounting subassemblies 8 also comprise a fastener 84 that can pass through the regulation hole 811 and can be inserted into the light body 1, so that fixed plate 81 is located corresponding to light body 1 in a fixed way. In such a case, fastener 84 is fixed onto the connecting position of light body 1, and fixed plate 81 can be driven to move corresponding light body 1 when fastener 84 is loosened. Of course, in other embodiments, the fixed plate 81 can also be provided with regulation holes 811, the top surface of light body 1 is provided with several fixed holes 19 in the slide direction of fixed plate 81, mounting subassemblies 8 also comprises a fastener 84 that can pass through regulation hole 811 and can be inserted into one fixed hole 19 to make fixed plate 81 fixed corresponding to light body 1. In such a case, by setting several fixed holes 19, the regulation scope of slide of fixed plates 81 corresponding to light body 1 can be enlarged. Further, to improve the connecting strength of engaging lugs 82 and fixed plates 81, the engaging lugs 82 and fixed plates 81 can be an integral strucure.

In addition, according to FIGS. 32-35, when the height between the downlight top and the connecting surface of fixed plate 81 and the mounting surface 18 is relatively great, and exceeds the effective clamping thickness scope of clamping piece 83, proposal 1 is adopted: Mounting subassemblies 8 also comprises an extension plate 85, and fixed plate 81, extension plate 85 and engaging lugs 82 are connected in sequence; Fixed plate 81 is provided horizontally and connects the extension plate 85, extension plate 85 is bent downward to the one side of mounting surface 18, and engaging lugs 82 are provided on one end of extension plate 85 away from the fixed plate 81. To improve the connecting strength of fixed plate 81, extension plate 85 and engaging lugs 82, fixed plate 81, extension plate 85 and engaging lugs 82 can form an integral structure. In addition, mounting subassemblies 8 can also further comprise engaging plates 86 that connect engaging lugs 82 and extend downward to one side of mounting surface 18. In such a case, fixed plate 81, extension plate 85, engaging lug 82 and engaging plate 86 can form an integral structure to enhance their connecting strength.

Figure 36:
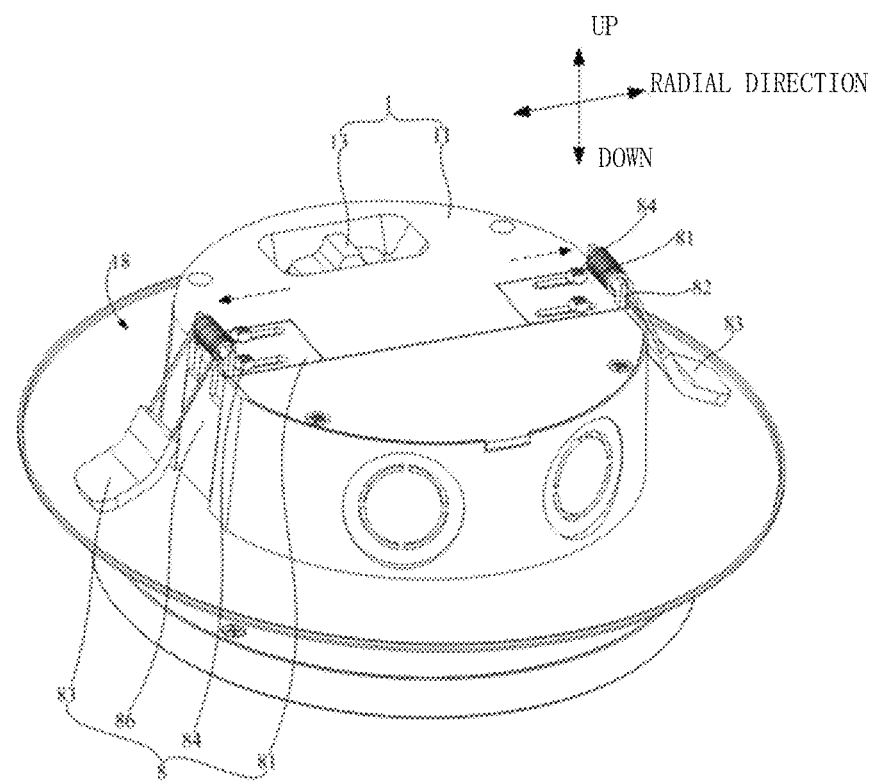
FIG. 36 is a schematic diagram showing the structure of another embodiment of a new-type downlight of the present disclosure.
Figure 37:
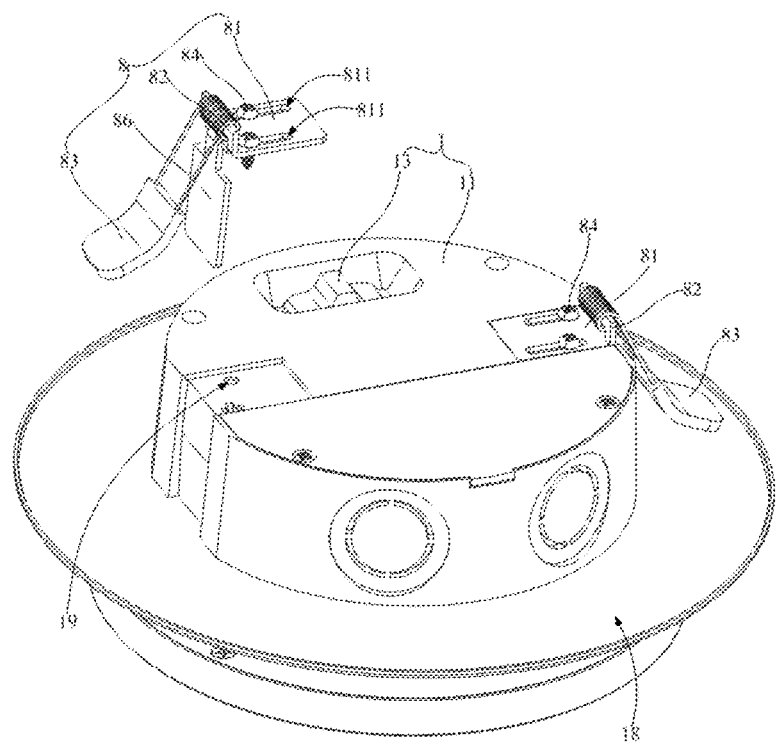
FIG. 37 is a schematic diagram showing the explosion structure of the light body and mounting subassemblies of the downlight in FIG. 36.
Figure 38:
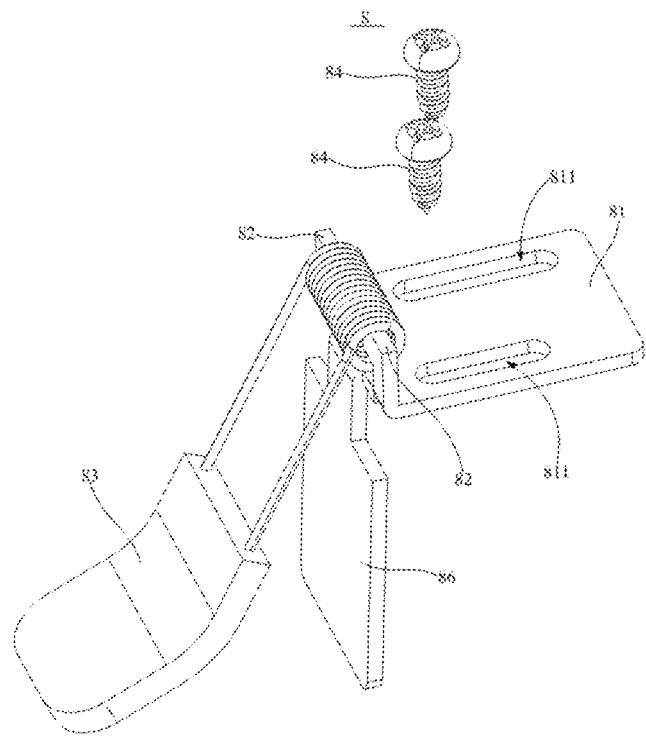
FIG. 38 is a schematic diagram showing the structure of the mounting subassemblies of the downlight in FIG. 36.

According to FIGS. 36-38, when the height between the downlight top and the connecting surface of fixed plate 81 and the mounting surface is relatively small, and exceeds the effective clamping thickness scope of clamping piece 83, proposal 2 is adopted: Mounting subassemblies 8 can also comprise an engaging plate 86, and a fixed plate 81 connect to engaging plate 86; fixed plates 81 are provided horizontally, engaging lugs are provided between fixed plate 81 and engaging plates 86, and engaging plates 86 is bent downward to one side of mounting surface 18. Further, to improve the connecting strength of fixed plate 81, engaging lugs 82 and engaging plate 86, and fixed plate 81, engaging lugs 82 and engaging plate 86 can form an integral structure.

Figure 39:
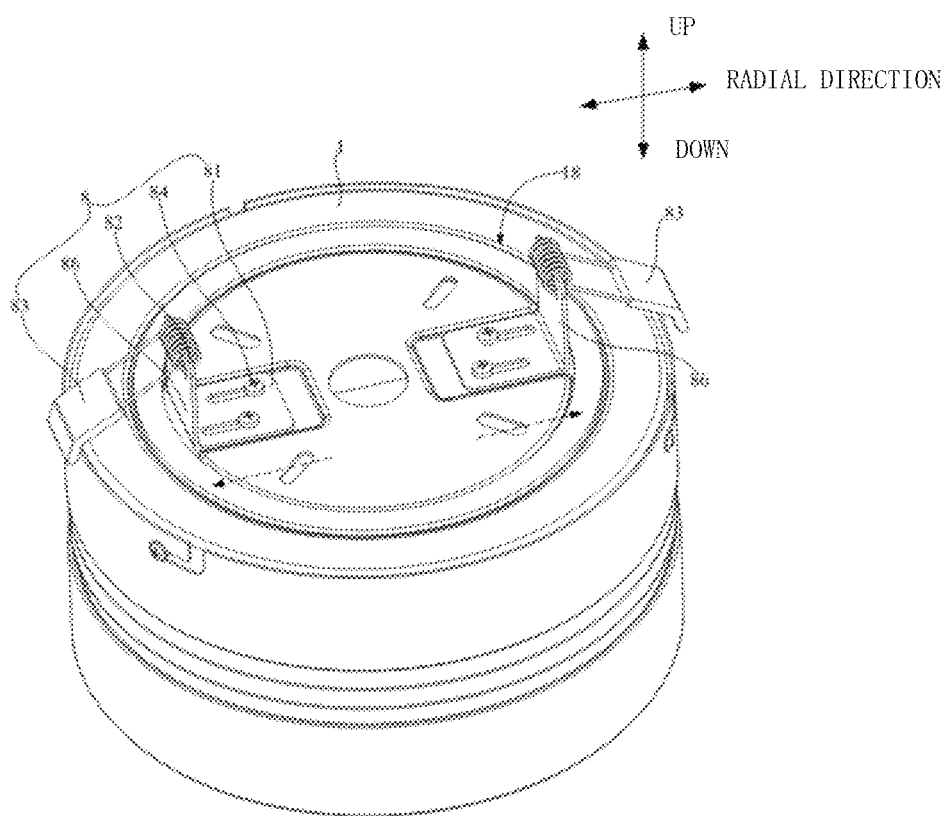
FIG. 39 is a schematic diagram showing the structure of another embodiment of a new-type downlight of the present disclosure.
Figure 40:
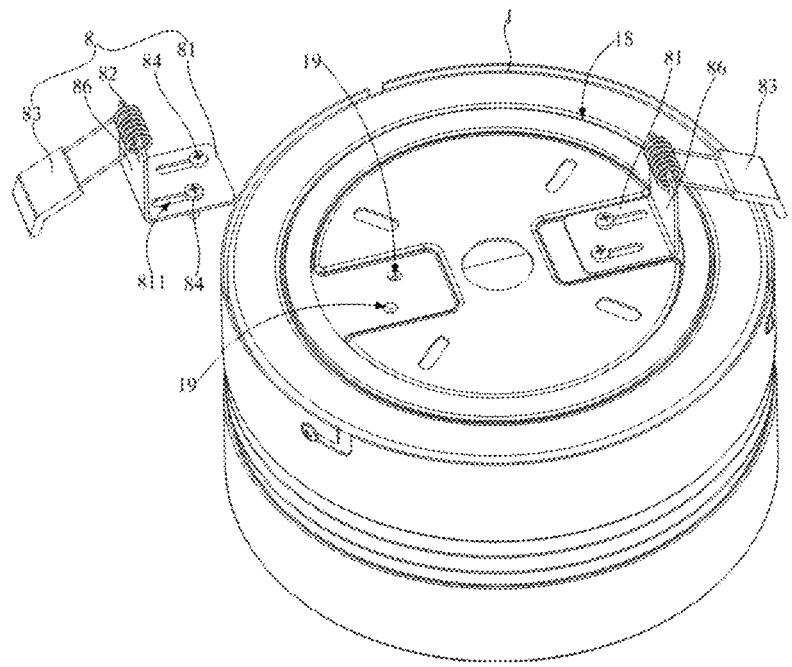
FIG. 40 is a schematic diagram showing the explosion structure of the light body and mounting subassemblies of the downlight in FIG. 39.
Figure 41:
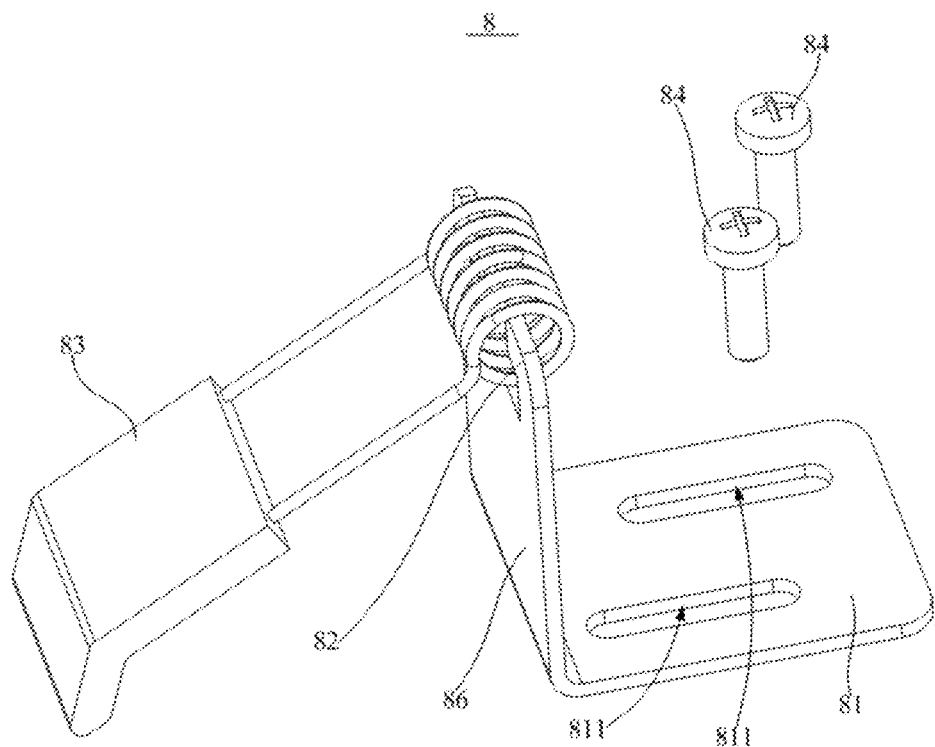
FIG. 41 is a schematic diagram showing the structure of the mounting subassemblies of the downlight in FIG. 39.

According to FIGS. 39-41, when the height difference between height between the downlight top and the connecting surface of fixed plate 81 and the height of the mounting surface 18 is smaller than the height of engaging lugs 82, or the height between the downlight top and the connecting surface of fixed plate 81 is smaller than the height of mounting surface 18, proposal 3 is adopted: Mounting subassemblies 8 also comprises an engaging plate 86, and fixed plate 81, engaging plate 86 and engaging lugs 82 are connected in sequence; Fixed plate 81 is provided horizontally and connects engaging plate 86, engaging plate 86 is bent upward, and engaging lugs 82 are provided on one end of engaging plate 86 away from fixed plate 81. Proposal 3 is applicable to the case where other types of lights are transformed into recessed downlights quickly, so that lights can be installed onto the ceiling or other external bearing part. Further, to improve the connecting strength of fixed plate 81, engaging lugs 82 and engaging plate 86, and fixed plate 81, engaging lugs 82 and engaging plate 86 can form an integral structure.

In the above embodiments, downlight comprises two mounting subassemblies 8 that are opposite to each other. In other embodiments, the quantity of mounting subassemblies 8 can increase to be applicable to installation of a large number of downlights.

In prior art, engaging lugs 82 are usually provided on light body 1 in a fixed way, and mounting subassemblies 8 need to be assembled with light body 1. Wherein, when clamping piece 83 is installed onto engaging lug 82, the spring port of clamping piece 83 is easy to scratch the surface of light body 1, so the defective ratio is high, and the assembly efficiency is low. By designing mounting subassemblies 8 into independent subassemblies, it is easy to realize connection between clamping piece 83 and engaging lugs 82, improve the assembly efficiency significantly; and mounting subassemblies 8 can be installed onto the top surface of light body 1 in a slide way, which enables that the opening size of downlight can be regulated, and the same type of downlight can be installed in different specifications of mounting holes, achieving good application effects.

The above description only present disclosures the preferred embodiments of the present disclosure, and it is not for this reason that the patent scope of the present disclosure is limited. Any equivalent structural transformation made by using the description of the present disclosure and the drawings, or direct/indirect application in other related technical fields under the inventive concept of the present disclosure is included in the patent protection scope of the present disclosure.

What is claimed is:

1. A ventilation-type UV light used for air sterilization and disinfection, the ventilation-type UV light comprising:
    a light body, an air guide structure arranged at bottom of a lamp body, a UV module, a fan and two air inlets; the air guide structure and the light body enclose to form a mounting space, the UV module is installed inside the mounting space; the fan is provided inside the air guide structure, a bottom of the air guide structure is provided with air outlets, the air inlets are provided on a periphery or bottom of the ventilation-type UV light in an encircling manner, and both the air inlets and the air outlets access the mounting space;
    wherein, air flows into the mounting space along the air inlets and then is discharged downward via the air outlets after being sterilized and disinfected by the UV module in the mounting space; and
    wherein the bottom of the fan is provided with a shielding part that prevents UV rays emitted by the UV module from being leaked.

2. The ventilation-type UV light as claimed in claim 1, wherein the air guide structure comprises a wind scooper and a baseplate, the wind scooper is a tubular structure with an opening at each end, a top port and a bottom port of the wind scooper access each other, the top port accesses the mounting space, the baseplate is provided at the bottom of the wind scooper, the corresponding the bottom port is provided with a downward the air outlet to make air that flows into the mounting space can pass through the top port and the bottom port and then can be discharged via the air outlet.

3. The ventilation-type UV light as claimed in claim 2, wherein three projections of the bottom port, the shielding part, and the top port are provided from largest to the smallest in descending order;
    and/or the wind scooper also comprises an air guiding plane provided between the top port and the bottom port, and the air guiding plane extends to the air outlet;
    and/or the wind scooper comprises a connecting part that is higher than the top port, and the inside of the connecting part is provided with a through-hole;
    and/or the fan is a centrifugal fan that enables air to flow into the fan from one end and flow out of the fan from the periphery, the centrifugal fan is provided inside the wind scooper horizontally, and the air inlets of the fan are provided corresponding to the top port;
    and/or the wind scooper and the baseplate are connected in a dismountable way;
    and/or the wind scooper is provided horizontally.

4. The ventilation-type UV light as claimed in claim 3, wherein when the bottom of the fan is provided with the shielding part, the air outlets are provided on the baseplate and between the periphery of the bottom port and periphery of the shielding part, and the air outlets are provided along the periphery of the shielding part in an encircling manner;

and/or the shielding part is an independent part, or a bottom lighting module or the middle structure of the baseplate.

5. The ventilation-type UV light as claimed in claim 4, wherein the ventilation-type UV light has a center line in an up-down direction, the center line passes through the light body, the air guide structure and the fan, the air inlets and/or the air outlets are provided around the center line;

and/or the air guide structure also comprises an indicator light, at least part of structure of the indicator light is exposed to the bottom surface of the air guide structure, and the indicator light is used for displaying the working status of the UV module.

6. The ventilation-type UV light as claimed in claim 5, wherein the light body and the air guide structure are connected in a dismountable way;

and/or the light body comprises a control box, a driving power supply and a dimmer switch, the dimmer switch is used for regulating the color temperature or power of the ventilation-type UV light;

and/or the inside of the mounting space is also provided with a reflective board, the reflective board is used for increasing reflection of UV rays emitted by the UV module.

7. The ventilation-type UV light as claimed in claim 6, wherein when the light body comprises the control box, the driving power supply and the dimmer switch, the dimmer switch comprises two opposite buckles, toggling part and plugging hole; the buckles comprise an extension arm and a stuck point; both the buckle and the plugging hole are provided on one end away from the toggling part; the control box is provided with a sliding hole, two the buckles are inserted into the sliding hole, the dimmer switch connects to the control box in a flexible way via the extension arm and stuck point of the dimmer switch; the driving power supply comprises a toggle switch inserted into the plugging hole, and the corresponding gear of color temperature or power can be regulated by sliding the toggling part.

8. The ventilation-type UV light as claimed in claim 2, wherein the air inlet is formed by the periphery of the light body and periphery of the air guide structure in an enclosing manner, enabling air to flow into the mounting space horizontally, obliquely upward or obliquely downward via the air inlet.

9. The ventilation-type UV light as claimed in claim 1, wherein the light body comprises a mounting subassembly at the bottom of the light body, the bottom of the mounting subassembly is provided with a groove with a downward opening, the air guide structure is inserted into the groove and encloses with the mounting subassembly to form the mounting space; and the mounting subassembly comprises a convex part and a lateral margin provided on the periphery of the convex part, the convex part and the lateral margin are of an integral structure, the convex part forms the groove with a downward opening, the air guide structure and the mounting subassembly enclose to form the mounting space and the air inlets, the air inlets are located on the lateral margin; and the baseplate is provided with a connecting column corresponding to the lateral margin, and the light body and the air guide structure are connected in a dismountable way via the connecting column and corresponding fasteners.

10. The ventilation-type UV light as claimed in claim 1, wherein the ventilation-type UV light is inserted into the mounting hole of an external bearing part, the mounting hole passes through the upper surface and lower surface of the bearing part, the ventilation-type UV light also comprises at least two mounting subassemblies, the light body comprises a mounting surface against the lower surface of the bearing part; and the mounting subassemblies comprise a fixed plate, engaging lugs and clamping pieces, the fixed plate is provided on the surface of the top of the light body horizontally in a slidable way and can be located for fixing corresponding to the light body, the engaging lugs and the fixed plates are directly or indirectly connected, the clamping pieces are elastic parts installed on the engaging lugs; when a downlight is installed inside the mounting hole, the clamping piece can be against the upper surface of the bearing part to fix the ventilation-type UV light onto the bearing part.

* * * * *